Figure 1:
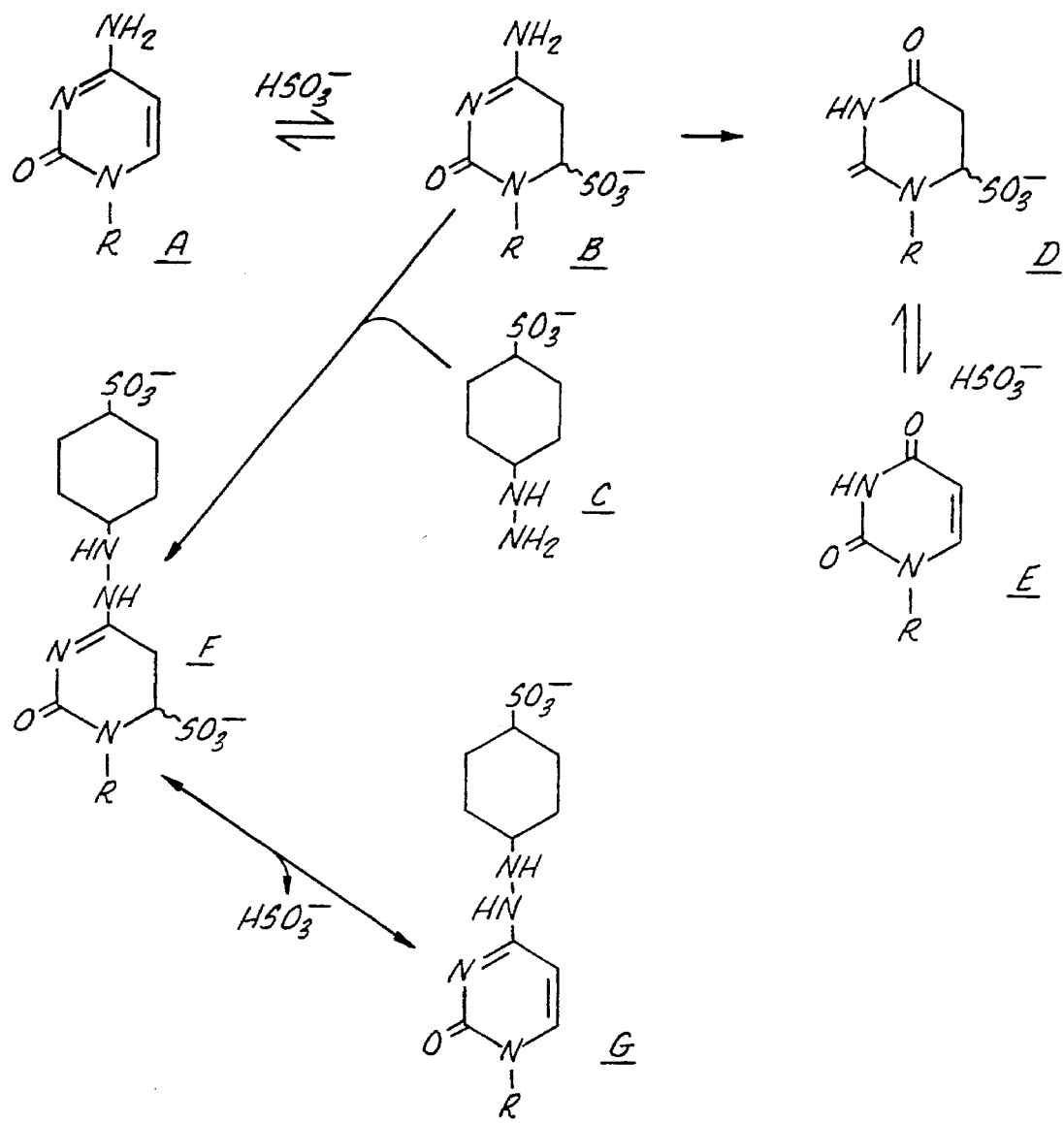

United States Patent [19]
Adams

[11] Patent Number: 5,552,541
[45] Date of Patent: Sep. 3, 1996

[54] HAPTENIC PROBES FOR DETECTING CAPTURE POLYNUCLEOTIDES

[75] Inventor: Craig W. Adams, Corona, Calif.

[73] Assignee: Beckman Instruments, Inc., Fullerton, Calif.

[21] Appl. No.: 541,143

[22] Filed: Jun. 20, 1990

[51] Int. Cl.$^6$ ............... C07H 21/04; C07H 21/00; C12Q 1/68

[52] U.S. Cl. ............... 536/22.1; 435/6; 436/501; 536/23.1; 536/24.1; 536/24.3; 536/24.31; 536/24.32; 536/24.33; 536/25.3; 935/19; 935/78; 935/81; 935/88

[58] Field of Search ............... 435/6, 7.1, 7.5, 435/7.7, 7.92; 436/501; 536/27, 22.1, 23.1, 24.1, 24.3–.33, 25.3

[56] References Cited

U.S. PATENT DOCUMENTS

| | | | |
|---|---|---|---|
| 4,490,473 | 12/1984 | Brunhouse | 436/518 |
| 4,547,569 | 10/1985 | Letsinger et al. | 536/29 |
| 4,699,876 | 10/1987 | Libeskind | 435/5 |
| 4,707,440 | 11/1987 | Stavrianopoulos | 435/6 |
| 4,711,955 | 12/1987 | Ward et al. | 536/29 |
| 4,828,979 | 5/1989 | Klevan et al. | 435/6 |
| 4,952,685 | 8/1990 | Stavrianopoulos | 536/27 |
| 4,963,477 | 10/1990 | Tchen | 435/6 |
| 4,968,602 | 11/1990 | Dattagupta | 435/6 |
| 5,013,831 | 5/1991 | Stavrianopoulos | 536/27 |

FOREIGN PATENT DOCUMENTS

| | | |
|---|---|---|
| 0146815 | 7/1985 | European Pat. Off. . |
| 0158758 | 10/1985 | European Pat. Off. . |
| 0244860 | 11/1987 | European Pat. Off. . |
| 0251527 | 1/1988 | European Pat. Off. . |
| WO91/19729 | 12/1991 | WIPO . |

OTHER PUBLICATIONS

Ghosh et al. (1989) Anal. Bioch., vol. 178, pp. 43–51.

Richardson et al. (1983) Nucleic Acids Research, vol. 11, No. 18, pp. 6167–6184.

Brown et al. (1982) Gene. vol. 20, pp. 139–144.

Levy, Robert B. et al., "Cell Mediated Lympholytic Responses . . . ", J. Immunology 127/2:523–528 (1981).

Herzberg, M., et al., "New concept in diagnostic procedures . . . " Chimica Oggi 69–71 (Nov. 1987).

Povernenny, A. M., et al. "Immunochemical Identification . . . " Mol. Immun. 16:313–326 (1979).

"A Chemical Method for Introducing Haptens onto DNA Probes", Keller, George H., et al., Anal. Biochem. 170, 441–450 (1988).

"p–Diazobenzoyl–biocytin: a new biotinylating reagent for DNA", Rothenberg, Jeffrey M., et al., Nucleic Acids Research, vol. 16, No. 14, 7197 (1988).

"A new biotinylating system for DNA using biotin aminocaproyl hydrazide and glutaraidehyde", Takahashi, T., et al., Nucleic Acids Research, vol. 17, No. 12, 4899 (1989).

"Labeling of DNA Probes with a Photoactivatable Hapten", Keller, George H., et al., Anal. Biochem.; 177, 392–395 (1989).

(List continued on next page.)

Primary Examiner—W. Gary Jones
Assistant Examiner—Ardin H. Marschel
Attorney, Agent, or Firm—William H. May; Janis C. Henry

[57] ABSTRACT

Nucleic acid probes and protein probes are disclosed. The nucleic acid probe comprises a probe polynucleotide, a charged hapten label, and a binding moiety. The protein probe comprises a probe protein, a charged hapten label and a binding moiety. The charged hapten label joint to the binding moiety can comprise a negatively charged sulfophenylhydrazine tag compound. Polyclonal antibodies and monoclonal antibodies with specific affinity for the charged hapten labels are disclosed as are hybridomas capable of making the monoclonal antibodies. Methods and kits are disclosed for making the nucleic acid probes, making the protein probes, detecting a capture polynucleotide of the nucleic acid probe and detecting a capture molecule of the protein probe.

7 Claims, 7 Drawing Sheets

OTHER PUBLICATIONS

H. Hayatsu et al., "The Modification of Nucleosides and Nucleotides. III. A Selective Modification of Cytidine with Semicarbazide," *Biochim. Biophys. Acta* 123, 445–457 (1966).

K. Kikugawa et al., "Modifications of Nucleosides and Nucleotides. V., A Selective Modification of Cytidylic Acids with Girard–P Reagent," *Biochim. Biophys. Acta* 134, 221–231 (1967).

R. Shapiro et al., "Reactions of Cytosine Derivatives with Acidic Buffer Solutions. II. Studies on Transamination, Deamination, and Deuterium Exchange," *Biochem.* 6(11), 3576–3582 (1967).

H. Hayatsu et al., "Reaction of Sodium Bisulfite with Uracil, Cytosine and Their Derivatives," *Biochem.* 9(14), 2858–2865 (1970).

R. Shapiro et al., "Bisulfite–catalyzed Transamination of Cytosine and Cytidine," *Biochem. Biophys. Res. Comm.* 40(4), 839–843 (1970).

E. I. Budowsky et al., "New Method of Selective and Rapid Modification of the Cytidine Residues," *FEBS Letters* 25(1), 201–204 (1972).

J. K. Inman et al., "Demonstration of a Simple Method for Reducing Losses of Tryptic Peptides During Automated Sequencing," Biochem. Biophys. Res. *Comm.* 46(6), 2075–2081 (1972).

M. Sono et al., "Role of Bisulfite in the Deamination and the Hydrogen Isotope Exchange of Cytidylic Acid," *J. Am. Chem. Soc.* 95(14), 4745 (1973).

P. W. Piper et al., "The Selective Reaction of Methoxyamine with Cytidine Residues in Mammalian Initiator Transfer Ribonucleic Acid," *Nucleic Acids Research* 1(1), 45–51 (1974).

R. Shapiro et al., "Deamination of Cytosine Derivatives by Bisulfite Mechanism of the Reaction," *J. of the American Chem. Society* 96(3), 906–912 (1974).

E. D. Verdlov et al., "Modification of Cytidine Residues with a Bisulfite—O–methylhydroxylamine Mixture," *Biochim. Biophys. Acta* 340, 153–165 (1974).

H. Hayatsu, "Reaction of Cytidine with Semicarbizide in the Presence of Bisulfite. A Rapid Modification Specific for Single–stranded Polynucleotide," *Biochem.* 15 (12), 2677–2681 (1976).

L. H. Schulman et al., "Attachment of Protein Affinity–labeling Reagents of Variable Length and Amino Acid Specificity to *E. coli* tRNA$^{fMet}$," *Nucleic Acids Research* 9(5), 1203–1217 (1981).

E. Fujimori et al., "Fluorescent–labeled Cross–links in Collagen: Pyrenesulfonylhydrazine," *Biochem.* 20, 4852–4855 (1981).

D. E. Draper, "Attachment of Reporter Groups to Specific, Selected Cytidine Residues in RNA Using a Bisulfite-catalyzed Transamination Reaction," *Nucleic Acids Research* 12(2), 989–1002 (1984).

R. P. Viscidi et al., "Novel Chemical Method for the Preparation of Nucleic Acids for Nonisotopic Hybridization," *J. Clin. Microbiol.* 23(2), 311–317 (1986).

J. J. Wadsley et al., "The Effect of pH on the Aggregation of Biotinylated Antibodies and on the Signal–to–noise Observed in Immunoassays Utilizing Biotinylated Antibodies," *J. Immuno. Methods* 103, 1–7 (1987).

A. Reisfeld et al., "Nonradioactive Hybridization Probes Prepared by the Reaction of Biotin Hydrazide with DNA," *Biochem. Biophys. Res. Comm.* 142(2), 519–526 (1987).

M. Pezzela et al., "In Situ Hybridization of Human Immunodeficiency Virus (HTLV–III) in Cryostat Sections of Lymph Nodes of Lymphadenopathy Syndrome Patients," *J. Med. Virology* 22, 135–142 (1987).

H. C. Hyman et al., "DNA Probes for Detection and Identification of *Mycoplasma pneumoniae* and *Mycoplasma genitalium*," *J. Clin. Microbiol.* 25(4), 726–728 (1987).

Chemiprobe® Kit Instruction Manual and Reference Guide (undated).

SulfoPROBE® Kit Technical Bulletin No. PROBE–2 (Aug. 1988).

HAPTENIC PROBES FOR DETECTING CAPTURE POLYNUCLEOTIDES

BACKGROUND

The present invention is directed to novel nucleic acid probes and protein probes. The invention is also directed to particular novel polyclonal and monoclonal antibodies useful for detecting the probes, and to novel hybridomas for making the monoclonal antibodies.

Nucleic acid probes, also called hybridization probes, allow specific polynucleotide sequences to be detected. Protein probes make possible detection of various compounds, such as proteins, steroids, carbohydrates, and nucleic acids that will undergo specific, usually noncovalent binding with the protein probe. When the protein probe is a labeled antibody, detection of a corresponding antigen is possible.

Nucleic acid probes can be used to detect specific polynucleotide sequences and can assist the diagnosis and treatment of numerous genetic disorders and diseases such as cystic fibrosis, muscular dystrophy, acquired immune deficiency syndrome (AIDS), hepatitis, herpes simplex, Epstein-Barr, and various viral infections such as those caused by cytomegalovirus and adenovirus.

Nucleic acid probes can also reveal genes coding antigens responsible for graft rejection. Genetic information useful in cancer oncogeny testing and forensic medicine can be obtained.

The hybridization probe or the protein probe can be made by labeling a polynucleotide or a protein with a detectable label in a modification or attaching reaction. Typically, the label is joined to a binding moiety before being attached to the polynucleotide or the protein. The binding moiety has a reactive group that functions to attach the label to the polynucleotide or to the protein. The label joined to the binding moiety is called a tag compound.

The hybridization probe can be contacted and incubated with another polynucleotide, called a capture polynucleotide, in a specific binding assay to determine if the two polynucleotides hybridize together. If the hybridization probe has been selected to include a polynucleotide, called the probe polynucleotide, which has at least one sequence or region substantially complementary to a sequence or region of the capture polynucleotide, then hybridization of the two polynucleotides occurs.

The protein probe can also be contacted and incubated with a specific binding partner in a specific binding reaction. Specific binding is generally strong but reversible, and does not normally lead to the formation or breaking of covalent bonds between or within members of the binding pair. Binding pairs can include antigen/antibody and receptor/receptor-binding molecule binding pairs.

Radioactive isotopes of atoms such as hydrogen ($^3H$), phosphorus ($^{32}P$), or iodine ($^{125}I$) are commonly used labels. Assays using radioactive labels require extensive safety precautions, expensive equipment and special waste treatment procedures often requiring a combination of federal, state, and local regulatory involvement. The instability of radioactive labels also results in high usage costs. Additionally, even with long exposure time, limited resolution is available in $^3H$ and $^{125}I$ autoradiography. Furthermore, the $^{32}P$ isotope is a hazardous isotope. Hence, there is a need for nonradioactive labels for nucleic acid and protein probes.

In typical nonradioactive indirect labeling methodologies, a hapten is attached to a probe polynucleotide to serve as the indirect label. Alternately, the hapten can function as the indirect label by being attached to a protein. Following hybridization, the hapten-labeled probe polynucleotide can be contacted with an anti-hapten antibody, or a similar specific binding partner for the hapten. The anti-hapten antibody can be labeled with a detectable moiety such as, for example, an enzyme, chemiluminescent compound, or fluorescent compound. Alternately, a second antibody to the anti-hapten antibody can have the detectable moiety.

A difficulty in finding nonradioactive labels suitable for use in indirect labeling schemes is the requirement that such labels be haptenic, that is, capable of inducing an immune response when coupled to a carrier. The hapten label must also be capable of binding to its corresponding antibody. The hapten label also needs to be small enough not to interfere with the hybridization reaction, yet large enough to be "seen" by the anti-hapten antibody.

Biotin and its derivatives have been used as nonradioactive probe labels. Hybridized biotinylated probe is typically detected by contacting biotin label with avidin or an anti-biotin antibody. The biotin label is usually conjugated to a reactive group such as a hydrazide capable of attaching to or modifying a nucleotide. Prior-art biotin labels have included PHOTOBIOTIN™ (N-[4-azido-2-nitrophenyl]-N'-[N-d-biotinyl- 3-aminopropyl]-N'-methyl-3-propanediamine); biotin succinimide ester (biotin-NHS); and biotin hydrazide.

PHOTOBIOTIN™ can modify probe polynucleotide in about fifteen minutes, but is very expensive. PHOTOBIOTIN™ has the additional disadvantages of being unstable and extremely light sensitive, making the modification reaction difficult to control. Biotin hydrazide and biotin succinimide ester are not as expensive as PHOTOBIOTIN™, but both require much longer modification reaction times. Modification with biotin succinimide ester is a two-step procedure, while biotin hydrazide requires from twenty-four hours to approximately two-and-one-half days for completion of the modification reaction.

In addition to considerations of expense, stability, and modification reaction time, a "stickiness" or aggregation problem is encountered with biotin labels. Stickiness refers to the situation wherein biotinylated antibodies and/or nucleic acid probes aggregate due to the change in the surface characteristics of normally charged polynucleotides conjugated to neutral (uncharged) biotin. The aggregation problem is encountered with all biotin labels, regardless of the labeling conjugate used in preparation of the labeled probe. Aggregation results in reduced solubility and lower reactivity during the modification reaction.

Nonradioactive labels other than biotin have been sought for incorporation into probes to address these problems. The nonradioactive label can also be useful as an alternate nucleic acid and protein probe label. When biotin alternative labels are used in conjunction with biotinylated probes, sandwich assays can be performed in a single step.

Two nonradioactive, nonbiotin haptenic labels have recently met with some success. One is N-acetoxy-N-2-acetylaminofluorene (AAF) and its 7-iodo-derivative (AAIF). AAF and AAIF modify guanine residues. Another is methoxyamine (also referred to as o-methylhydroxylamine, methoxylamine, α-methylhydroxylamine, and hydroxylamine methyl ether). Commercial kits using methoxyamine-labeled probes are available from Sigma Chemical Company, St. Louis, Mo. (SulfoPROBE™), FMC Bio-Products, Rockland, Md. (CHEMIPROBE™), and Orgenics, Ltd., Israel (CHEMIPROBE™).

Neither of these two labels completely overcomes the problems associated with biotin labels. AAF is unstable. Methoxyamine is more stable but it is not very soluble, resulting in lower reactivity during the labeling process and less effective alleviation of the "stickiness" problem typically encountered with biotin labels. Both AAF and methyoxyamine are carcinogenic and must therefore be used with considerable caution.

What is needed therefore is a label for nucleic acids probes and protein probes that is: (1) haptenic; (2) stable; (3) reactive (for ease of labeling); (4) soluble (for both ease of labeling and to alleviate the "stickiness" problem); (5) noncarcinogenic; (6) nonradioactive; and (7) inexpensive.

SUMMARY

A label according to the present invention meets these needs. The label can be attached to a polynucleotide to make a hybridization probe. The hybridization probe is capable of hybridizing with a capture polynucleotide. The label can also be attached to a protein to make a protein probe. The protein probe can bind to a variety of specific binding partners.

Definitions

The following definitions are provided in order to facilitate an understanding of the present invention. To the extent that the definitions may vary from meanings within the art, the definitions below are to control.

The term "probe" can mean a hybridization probe or a protein probe.

"Hybridization probe" means a polynucleotide attached to a charged hapten label. The charged hapten label is attached to the polynucleotide by a binding moiety. A label joined to a binding moiety forms a "tag" compound.

The term "polynucleotide" is used interchangeably with the term "nucleic acid" and includes all oligonucleotides.

"Probe polynucleotide" is the polynucleotide of the "hybridization probe" and refers to a single-stranded polynucleotide fragment or strand. The structure of a probe polynucleotide can be known or unknown. The probe polynucleotide can be either single-stranded DNA or RNA.

The term "capture" polynucleotide means a polynucleotide with which the probe polynucleotide can hybridize.

The term "target" polynucleotide means a polynucleotide from or in a test sample. A target polynucleotide is an "unknown" polynucleotide.

The term "reference" polynucleotide means a "known" polynucleotide. A known polynucleotide means a polynucleotide from a known organism or a polynucleotide whose structure has been at least partly characterized.

The target polynucleotide or the reference polynucleotide can be used as the probe polynucleotide by being attached to the charged hapten label.

A "protein probe" comprises a protein attached to a charged hapten label. The charged hapten label is attached to the protein by a binding moiety.

"Probe protein" is the specific binding protein of a protein probe. The structure of a probe protein can also be known or unknown.

The term "capture molecule" means a molecule that can specifically bind with the probe protein.

Hybridization Probes

A hybridization probe according to the present invention has at least three parts. The three parts are a probe polynucleotide, a charged hapten label and a binding moiety.

The probe polynucleotide has at least one sequence or region substantially complementary to at least one sequence or region of a capture polynucleotide. The probe polynucleotide and the capture polynucleotide are therefore capable of hybridizing to each other. The probe polynucleotide can be either DNA or RNA and preferably has at least one cytosine base. The cytosine base can be transaminated by the preferred binding moieties of the invention in an attaching or modification reaction.

The charged hapten label is capable of being detected by an immunological reaction between the label and an antibody specific to the charged hapten label. Preferably the charged hapten label bears a net negative charge because of the advantages, such as increased solubility, that a net negative charge brings. Additionally as will be readily appreciated by those skilled in the art, antibody detection of positively charged hapten labels can be difficult. Preferably the hapten label is a negatively charged substituted phenyl group, and more preferably a carboxylate-substituted or a sulfonate-substituted (i.e., $SO_3$-substituted) phenyl group.

The binding moiety functions to attach the charged hapten label to the probe polynucleotide or to the probe protein. A binding moiety that contains a nucleophilic group can be reactive with modification-resistant polynucleotides. The binding moiety can be selected from the group consisting of hydroxylamines, hydrazines, hydrazides, hydrazones, oximes, carbazides, carbazones, primary amines, secondary amines, tertiary amines, amides and their derivatives. The preferred binding moiety is a hydrazine. Hydrazines are reactive with cytosine bases and a hydrazine-containing binding moiety can be used to modify the cytosine base of a polynucleotide.

The hybridization probe and the protein can also have a "spacer" component. The spacer component is disposed between the binding moiety and the charged hapten label and acts to spatially separate the charged hapten label from the probe polynucleotide, or in the case of a protein probe, from the probe protein. Separation can help reduce steric interference by the probe polynucleotide or the probe protein during an immunological reaction between the charged hapten label and an antibody specific to the label.

The spacer compound is of a sufficient size to provide the desired separation of the charged hapten label from either the probe polynucleotide or the probe protein.

A preferred hybridization probe is a 4-hydrazinobenzenesulfonate anion compound covalently attached through its hydrazine terminus to the 4-position of a cytosine base of single-stranded nucleic acid. This nucleic acid probe can be made under mild conditions and its use allows detection of picogram amounts of capture polynucleotide.

The hybridization or protein probe can have one or more additional labels, such as a biotin label. An additional label can provide an additional detectable site and thereby help reduce noise or background signal.

Another aspect of the invention is directed to a method for making the hybridization probe. The method comprises selecting the probe polynucleotide, selecting the charged hapten label joined to the binding moiety, attaching the binding moiety to the probe polynucleotide in an attaching reaction to thereby make the hybridization probe, and stopping the attaching reaction with a stopping compound.

A method for detecting the capture polynucleotide comprises mixing the hybridization probe and the capture polynucleotide, incubating the mixture to allow the hybridization reaction to take place between the capture polynucleotide and the hybridization probe, separating the hybridized from nonhybridized probe, and detecting the hybridized or nonhybridized probe. The detection means can be immunological detection means using an antibody specific to the charged hapten label of the hybridization probe.

Antibodies and Hybridomas

Additional aspects of the invention include polyclonal antibodies, monoclonal antibodies and hybridomas. The polyclonal and monoclonal antibodies have a specific binding affinity for the preferred haptenic sulfophenyl label. The antibodies can be IgG isotype antibodies. The hybridomas are capable of making monoclonal antibodies with specific affinity for the preferred haptenic sulfophenyl compound. The hybridomas can be hybrids of mouse spleen cells immunized with a sulfophenyl antigen and mouse myeloma cells.

Protein Probes

A protein probe according to the present invention has at least three parts. The three parts are a probe protein, a charged hapten label and a binding moiety. The probe protein can undergo a specific affinity binding reaction with a capture molecule. The charged hapten label can be detected by an immunological reaction between the charged hapten label and an antibody specific to the label. The binding moiety attaches the charged hapten label to the probe protein.

Kits

The present invention also includes within its scope various kits. A kit for making the hybridization probe and for detecting the charged hapten label includes the charged hapten label, the binding moiety, means for catalyzing the attaching reaction of the binding moiety to the probe polynucleotide, and the antibody specific to the charged hapten label.

A kit for making the protein probe and for detecting the capture molecule comprises the charged hapten label, the binding moiety, means for catalyzing the attaching reaction of the binding moiety to the probe protein, and the antibody specific to the charged hapten label.

The present invention satisfies the prior-art need for a nucleic acid label and a protein probe label that, when joined to a binding moiety, is soluble, stable, reactive, haptenic, nonradioactive and inexpensive. These characteristics result in a label-binding moiety conjugate (tag compound) that rapidly attaches to single-stranded polynucleotide or protein under mild conditions and that allows detection of small amounts of capture polynucleotide and capture molecule.

DRAWINGS

These and other features, aspects, and advantages of the present invention will become better understood from the following description, the appended claims, and the accompanying drawings where:

FIG. 1 illustrates a sulfite-catalyzed attaching reaction of sulfophenylhydrazine to a cytosine base.

Figure 2:
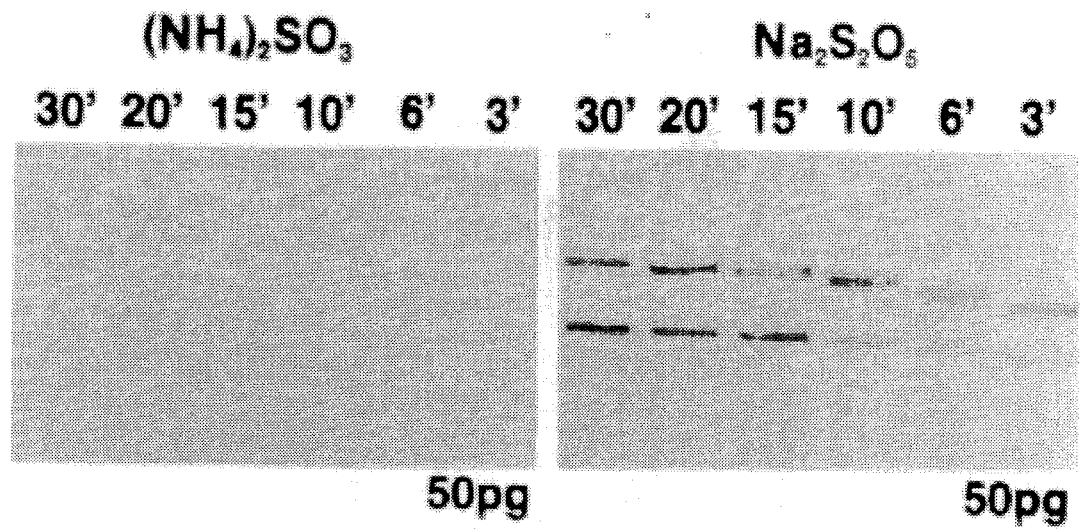
Figure 2:
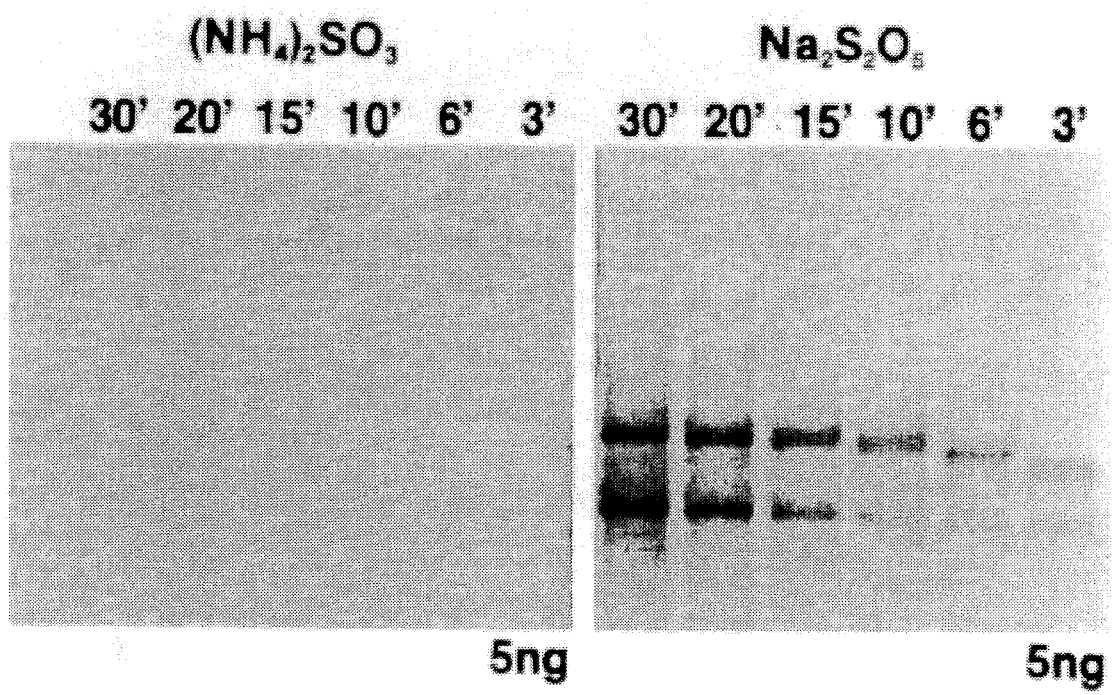

FIG. 2 provides the results of comparative studies of ammonium sulfite and sodium bisulfite catalysis of DNA modification by sulfophenylhydrazine at pH 4.5 for times between three minutes and thirty minutes.

Figure 3:
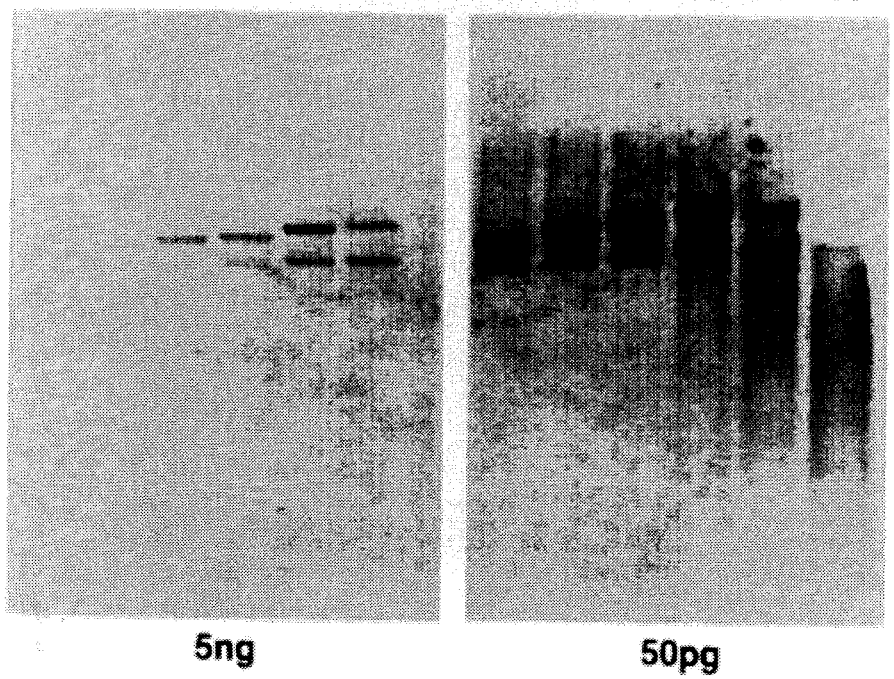

FIG. 3 provides the results of comparative studies of ammonium sulfite and sodium bisulfite catalysis of DNA modification by sulfophenylhydrazine at six temperatures between 40° C. and 90° C.

Figure 4:
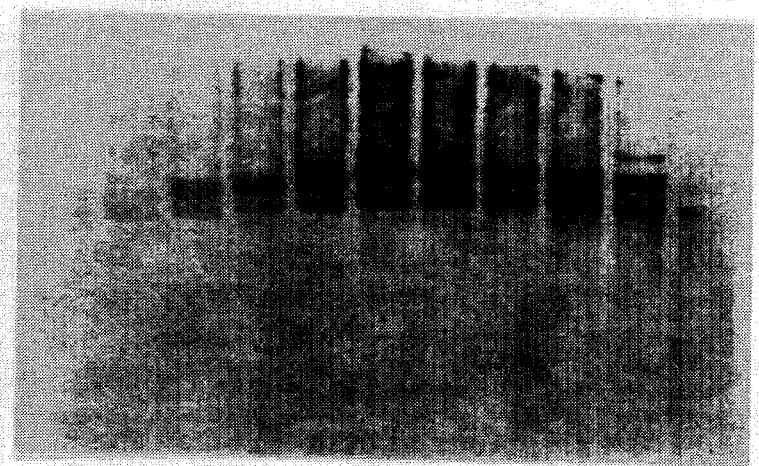

FIG. 4 provides the results of the effect of changing pH upon the modification of DNA by sulfophenylhydrazine at 80° C.

Figure 5:
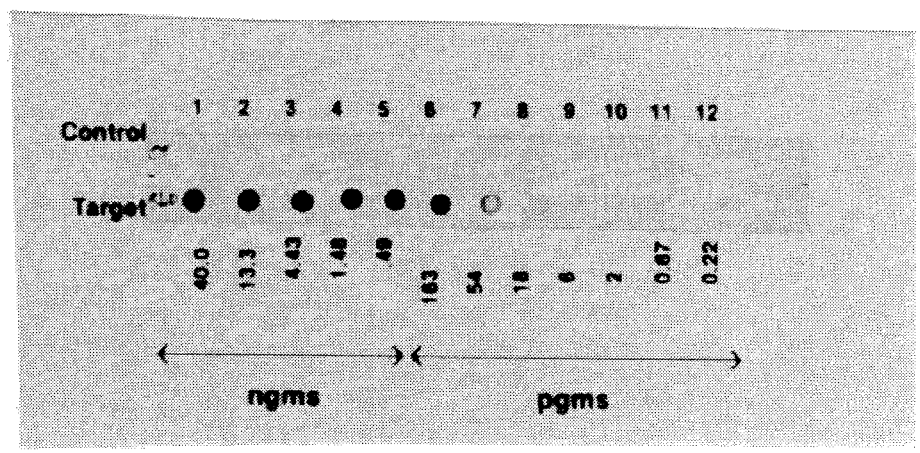

FIG. 5 provides the results of the sensitivity of an SPH-labeled hybridization probe.

Figure 6:
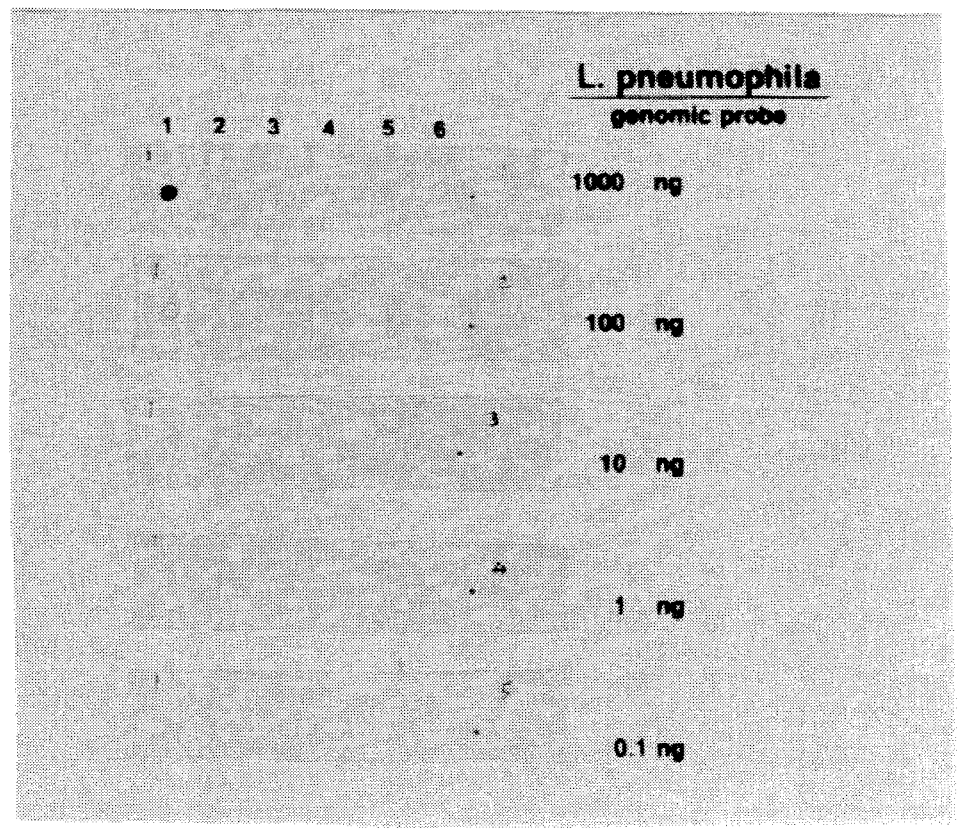

FIG. 6 provides the results of the detection of Legionella pneumophila using an SPH-labeled hybridization probe.

Figure 7:
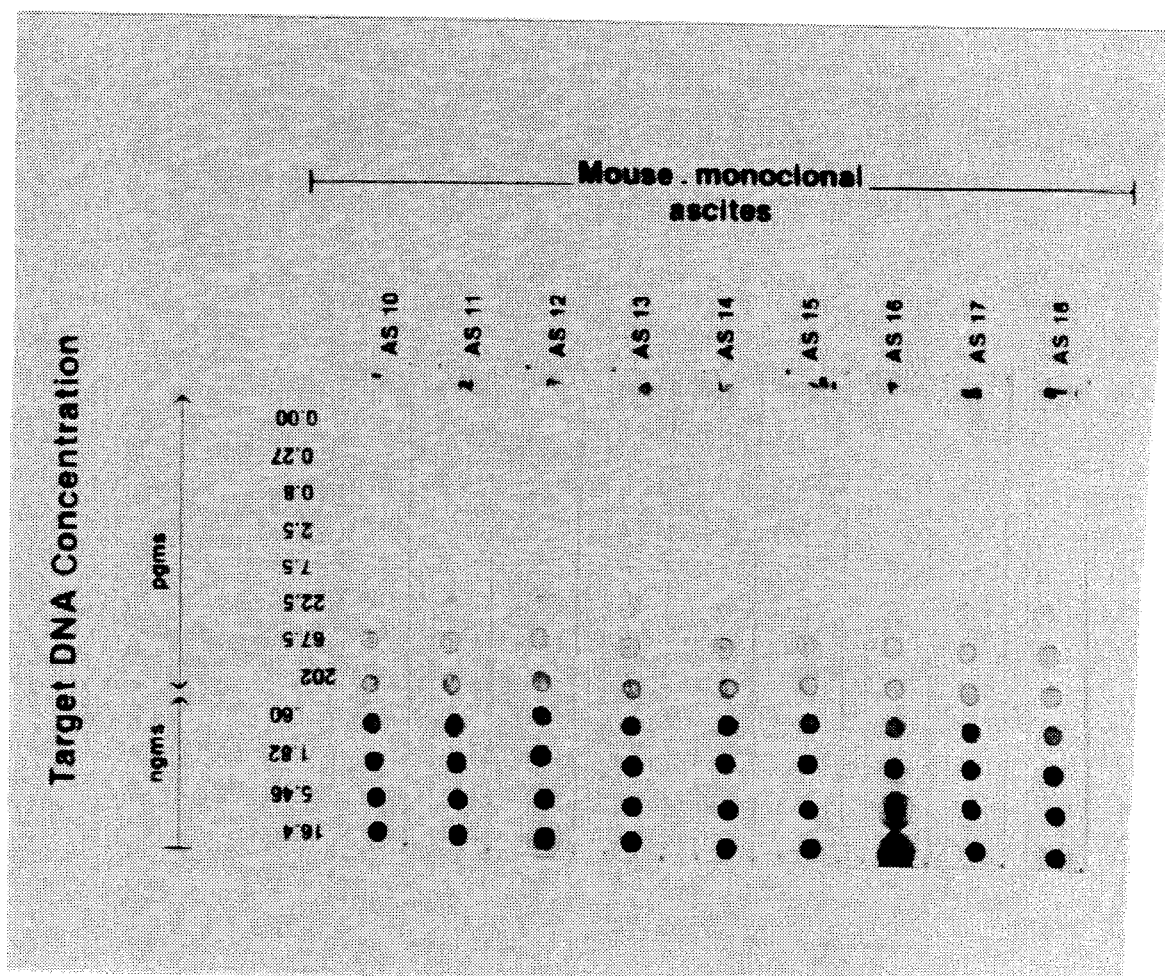

FIG. 7 provides the results of comparative studies of the affinities of the monoclonal antibodies from nine different hybridoma cell lines for a haptenic sulfophenyl label of a hybridization probe.

Figure 8:
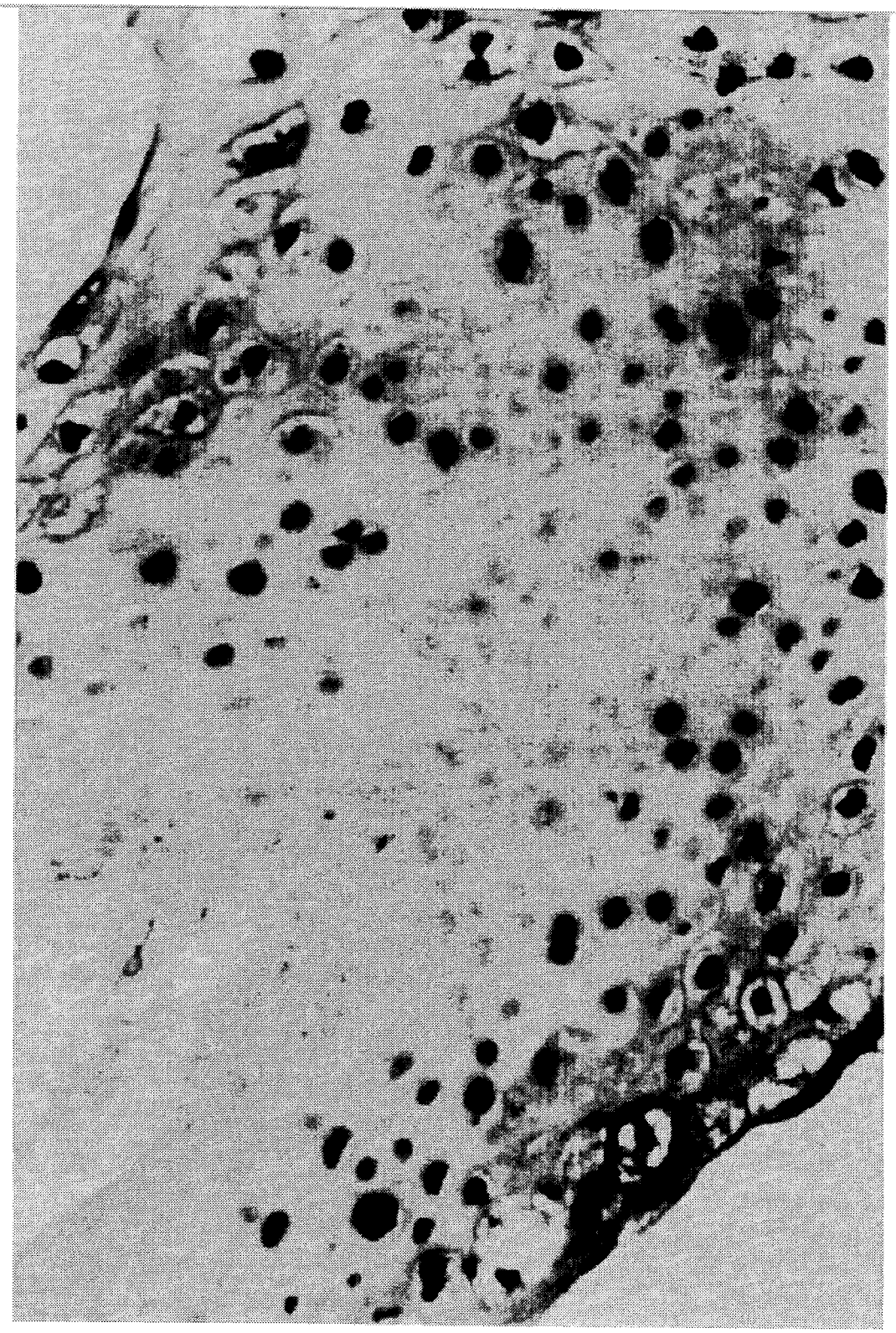

FIG. 8 provides the results of in situ detection of HPV 6 DNA in a human cervical biopsy tissue specimen using a sulfophenyl-labeled nucleic acid probe.

Figure 9:
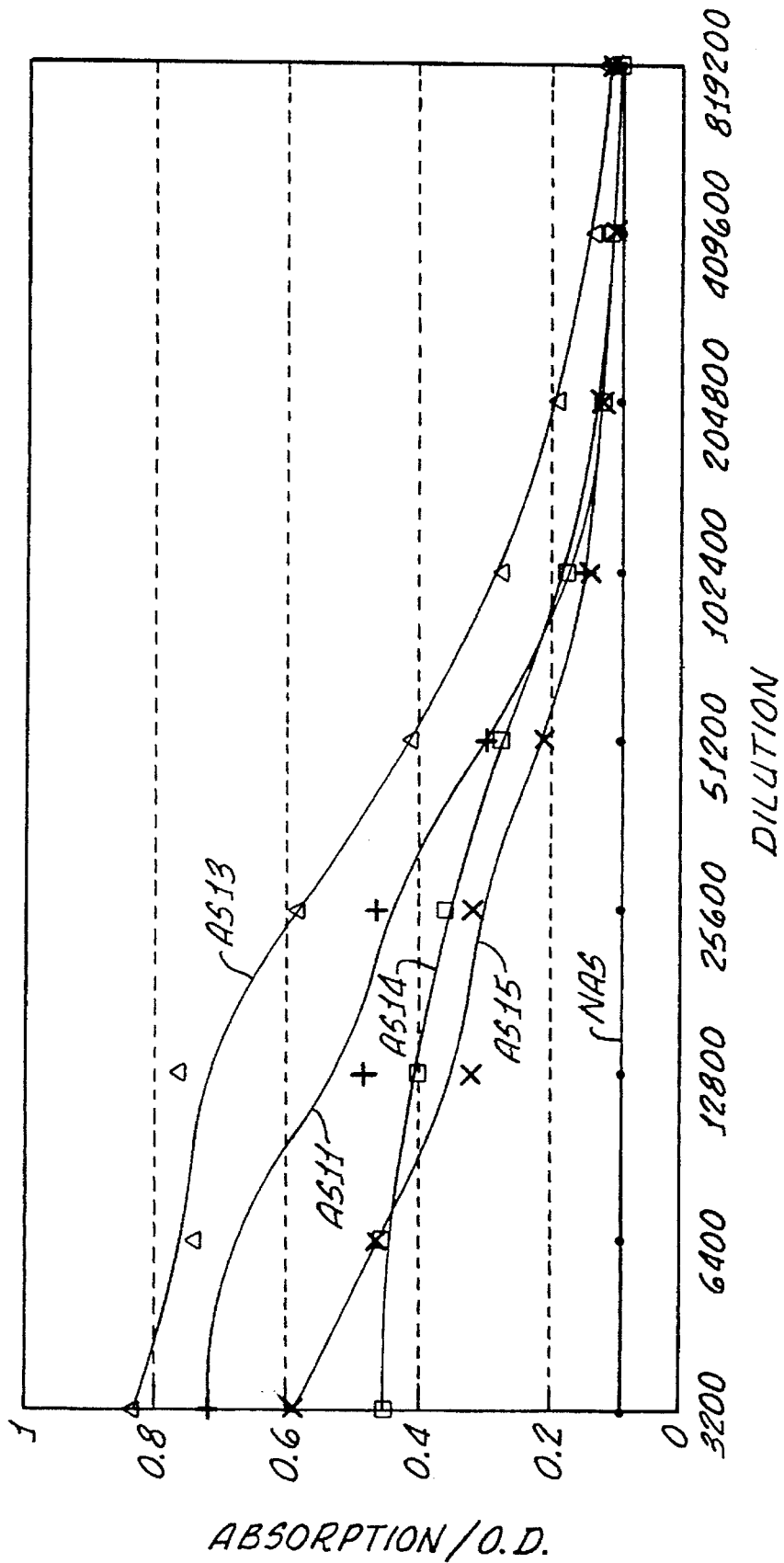

FIG. 9 graphically shows the specific affinity of mouse monoclonal antibodies for a sulfophenyl label of a protein probe.

DESCRIPTION

The present invention is based on the finding that certain compounds can function as superior nonradioactive haptenic labels for labeling polynucleotides. The labeled polynucleotides can be used as nucleic acid probes. Nucleic acid probes, or hybridization probes as they are also called, can be used to detect specific polynucleotide sequences. Specific polynucleotide sequences in a variety of test samples can be detected. Test samples include for example tissue specimens, serum, plasma, urine, saliva, cerebrospinal, amniotic and various other physiological fluids. Additionally, the nonradioactive haptenic labels of the present invention can be used to label proteins for use as protein probes.

Hybridization Probes

A hybridization probe of the present invention comprises a probe polynucleotide, a charged hapten label, and a binding moiety. The probe polynucleotide has at least one nucleotide sequence substantially complementary to at least one polynucleotide sequence of a capture polynucleotide, thereby enabling the two polynucleotides to hybridize together. The charged hapten label is capable of being detected by an immunological reaction between the label and an antibody specific to the label. The binding moiety functions to attach the charged hapten label to the probe polynucleotide.

The probe polynucleotide can be DNA or RNA and is preferably a single-stranded nucleic acid. The attaching reaction whereby the label is attached to the probe polynucleotide is more difficult with a double-stranded nucleic acid.

Preferred labels are charged at neutral pH, soluble in aqueous solution, and haptenic. A charge assists aqueous solubility which is desired to help obtain a fast modification reaction. The preferred hapten labels are negatively charged. A negative charge has been found to help reduce the "stickiness" or aggregation problem encountered with neutral or positively charged labels. A preferred label is a haptenic, anionic sulfophenyl compound, commercially available and generally stable at room temperature.

The binding moiety functions to attach the label to either the probe polynucleotide or to a probe protein of the protein probe. Preferably, the binding moiety comprises a nucleophilic binding moiety because some nucleophilic binding moieties can modify nucleic acids in an attaching reaction. A variety of nitrogenous, nucleophilic compounds suitable for use as binding moieties are readily available.

The binding moiety can be selected from the group consisting of hydroxylamines, hydrazines, hydrazides, hydrazones, oximes, carbazides, carbazones, primary amines, secondary amines, tertiary amines, amides and derivatives thereof. These compounds vary in the strength of their "nucleophilicity." The preferred nitrogenous nucleophilic binding moiety is a hydrazine because of the reactivity of hydrazines with modification-resistant polynucleotides.

The charged hapten label covalently joined to the binding moiety forms a tag compound. Preferably, the charged hapten label and the binding moiety are at opposite ends of the tag compound to prevent their interaction and to reduce steric hindrance during an immunological detection reaction of the charged hapten label.

Between the label and the binding moiety of the tag compound there can be an optional "spacer" compound. The spacer can be almost any compound that can be disposed between the charged hapten label and the binding moiety. The spacer compound functions to separate the label from the probe polynucleotide after attachment of the label to the probe polynucleotide. An example of a suitable spacer is a linear chain of from about two to about fifteen carbon atoms. By separating the label from the probe polynucleotide, the spacer compound can assist reduction of steric hindrance by the probe polynucleotide during an immunological detection of the label.

Examples of suitable charged hapten labels joined to hydrazine binding moieties are:

1. 4-hydrazinobenzoic acid anion;

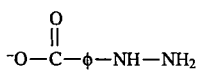

2. 4-(hydrazinosulfonyl) benzoic acid anion;

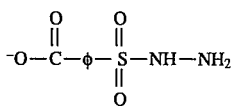

3. Sulfophenylhydrazine anion;

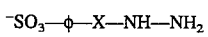

where φ is a phenyl group and X is a spacer compound.

A preferred charged hapten label joined to a binding moiety is a sulfophenylhydrazine compound. A preferred sulfophenylhydrazine compound comprises a haptenic, anionic sulfophenyl label covalently bound to a terminal hydrazine binding moiety. A highly preferred sulfophenylhydrazine compound is a 4-hydrazinobenzenesulfonate anion, referred to as "SPH." SPH has the following structure:

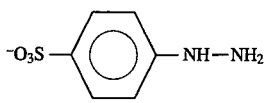

Use of SPH has many advantages. SPH is haptenic, inexpensive, stable, reactive with certain proteins and modification-resistant polynucleotides, available commercially, believed to be noncarcinogenic, nonradioactive, and has high aqueous solubility. Additionally, SPH can be stored for long periods at room temperature. The reactivity of the hydrazine terminus of SPH with cytosine bases allows a cytosine base-containing polynucleotide to be labeled with SPH in an attaching or modification reaction in ,less than about thirty minutes.

Another advantage of use of SPH as the label is that only minimal purification of the probe polynucleotide prior to modification with SPH is required. Minimal purification is sufficient because of the specificity of the SPH-cytosine modification reaction. The particular reaction specificity of SPH for cytosine reduces nonspecific labeling of fatty acids, carbohydrates and other compounds. Typically, five minutes on a spin column gives sufficient purification.

A further advantage of use of SPH is that SPH is soluble in aqueous solution at room temperature in concentrations less than one molar (i.e., about 50 mM) up to multiple molar concentrations (i.e., about 8M). The high aqueous solubility is believed due to the presence of the anionic sulfophenyl label component. High aqueous solubility allows for high levels of polynucleotide modification without the significant aggregation (i.e., "stickiness") problems known to occur with biotinylated probes.

Method for Making the Hybridization Probe

A method for making the hybridization probe capable of hybridizing with the capture polynucleotide comprises first selecting the probe polynucleotide, the charged hapten label, and the binding moiety. Preferably, the selected charged hapten label and binding moiety are covalently bound to each other as a tag compound. The next step is attaching the binding moiety of the tag compound to the probe polynucleotide in an attaching or modification reaction, followed by stopping the attaching reaction with a stopping compound.

The attaching reaction can be carried out in a suitable container by adding a solution of the probe polynucleotide to a solution of the charged hapten label joined to the binding moiety. Typically, the attaching reaction is stopped by the stopping compound, preferably after about thirty minutes or less. An attaching reaction of thirty minutes or less allows a sufficient number of the charged hapten labels to attach to the probe polynucleotide so that the labels can be easily detected by an immunological detection means. Continuing the attaching reaction for more than about thirty minutes can result in an excess amount of nonspecific labeling by the charged hapten label. Nonspecific labeling appears as "noise" or signal interference upon applying the detection means. Noise can make detection of the capture polynucleotide more difficult.

Additionally, continuing the attaching reaction for more than about thirty minutes can interfere with base pairing during the hybridization reaction. Base pairing can be interfered with due to an excessively large number of charged hapten labels that can attach to the probe polynucleotide.

Optimally, the attaching reaction is catalyzed by a sulfite or bisulfite salt. The salt can be an aqueous solution of a sodium bisulfite. The results presented in FIG. 2 indicate sodium bisulfite is superior to ammonium sulfite as the attaching reaction catalyst.

The attaching reaction can proceed by attaching the binding moiety to any of a number of different possible attachment sites on the probe polynucleotide. The binding moiety can be attached to a terminal phosphate group of the probe polynucleotide, such as a terminal 5' phosphate. A method to accomplish such an attachment is set forth by B.C.F. Chu et al. in "Derivatization of Unprotected Polynucleotides," *Nucleic Acids Research*, 11(18), 6513–6529, (1983), although any methodology known to those skilled in the art for accomplishing such an attachment can be used.

Alternatively, the binding moiety can be attached to a 3' terminus of an RNA molecule. A method to accomplish this type of attachment is set forth by F. Hansske et al. in "Modification of the 3' Terminus of tRNA by Perodate Oxidation and Subsequent Reaction with Hydrazides, "Methods in Enzymology, 59(10), 172–181, (1979), although any methodology known to those skilled in the art for accomplishing such an attachment can be used.

A variety of stopping compounds can be used. For example, the stopping compound can stop the attaching reaction by raising the pH of the reaction solution. A Tris buffer solution can be used as the pH-raising stopping compound. Generally, the pH is raised to at least about pH 7 to stop the attaching reaction.

Alternately, the stopping compound can be a blocking agent that stops the attaching reaction by reacting with the binding moiety of the tag compound to block the binding moiety and prevent further attaching reaction. The blocking agent can be an electrophilic compound such as an aldehyde or an anhydride. Suitable compounds include cinnam-aldehyde, succinic, salicylic acid and N-hydroxysuccinic amine ester anhydrides. These compounds are suitable because they can rapidly block the binding moiety. A most preferred blocking agent is succinic anhydride.

An advantage of use of an electrophilic blocking agent is that no purification of the probe polynucleotide is required prior to carrying out the attaching reaction. No purification of the probe polynucleotide is required because the electrophilic compound has a high reaction specificity for the binding moiety. For example, succinic anhydride specifically blocks the hydrazine binding moiety to the exclusion of many other compounds. Hence, the need to remove carbohydrates, proteins, etc., in a purification step is substantially eliminated.

FIG. 1 provides a postulated attaching reaction chemistry for SPH with the cytosine base in a sulfite catalyzed attaching reaction. In FIG. 1: A represents the cytosine base of the probe polynucleotide R; B is the cytosine base with a sulfonate group attached at the six-carbon-position; C is the SPH tag compound; D and E are equilibrium species of B; and E and G represent polynucleotide probe equilibrium products resulting from the attaching reaction.

As illustrated by FIG. 1, when SPH transaminates or modifies a cytosine base in an attaching reaction, the hydrazine binding moiety covalently attaches to the four-carbon-position of cytosine by replacing or transaminating the four-carbon amine of the cytosine base. The polynucleotide probe reaction products can bear more than one negative charge. Thus, in addition to the negatively charged sulfone on the sulfophenyl at the 4-position of the cytosine base, there can also be, depending upon the equilibrium conditions of the solution, a negatively charged sulfone group at the six-position of the cytosine base, as shown by species F.

The attaching reaction with sulfophenylhydrazine can be completed in less than about thirty minutes. As little as three minutes allows a number of detectable SPH tag compounds to attach to cytosine bases, as provided for in FIG. 2. An attaching reaction of about ten minutes is preferred as allowing enough sulfophenyl labels to attach for rapid detection of the sulfophenyl label without significant noise and base pairing problems.

The attaching reaction with SPH can be completed quickly because of the solubility and reactivity of SPH. The rate of an SPH attaching reaction can be increased by raising the reaction solution temperature up to at least about 40° C. and preferably up to about 90° C. Most preferred is an attaching reaction solution temperature of about 80° C. Additionally, a higher temperature can help to prevent nucleic acids forming double-stranded regions. Preferably, the attaching reaction takes place with single-stranded probe polynucleotides because the SPH attaching reaction is specific to single-stranded nucleic acids.

FIG. 3 provides the results of a study of the effects of temperature on the SPH modification of single-stranded M13 DNA on a nitrocellulose filter after reaction with color-developing reagents. The attaching reaction was carried out at the 6 different temperatures (40° C., 50° C., 60° C., 70° C., 80° C. and 90° C.). Because of the decreased reaction rate of the ammonium sulfite solution 100-fold more DNA was loaded onto the agarose gel for this reaction (5 ng DNA for ammonium sulfite versus 50 pg DNA for sodium bisulfite). Both attaching reactions were carried out for 15 minutes prior to being stopped by adding a stopping solution comprising 9 volumes of 1.0M Tris pH 8.5. An enzymatic, colorimetric-based detection was then carried out. FIG. 3 indicates a consistent increase in the aggressiveness of the labeling reaction with increasing temperature and that about 80° C. appears to be an optimal SPH modification reaction temperature.

As set forth in FIG. 4, the pH can also affect the rate and efficiency of the modification reaction. FIG. 4 provides the results of a study of the effects of pH on the sodium bisulfite-catalyzed SPH modification of single-stranded M13 DNA on a nitrocellulose filter after reaction with color-developing reagents. The attaching reaction was carried out at the 11 different pH values shown in the Figure. Fifty picograms of the DNA were used in each attaching reaction by loading this amount of DNA onto the agarose gel. The attaching reactions were carried out at 80° C. for 15 minutes before adding the stopping compound. According to the results evident from FIG. 4, the pH of the attaching reaction is preferably about 3 to about 6, more preferably about 4 to about 5, and most preferably about pH 4.5.

Analytical Methods Using the probe

An analytical method using the hybridization probe comprises mixing the hybridization probe and a capture polynucleotide, incubating the mixture to allow a hybridization reaction to take place between the two polynucleotides, separating hybridized probe from nonhybridized probe, and detecting the label of either the hybridized or nonhybridized probe. If the capture polynucleotide is double-stranded, it is denatured before the mixing step to obtain single-stranded capture polynucleotide. The hybridization reaction occurs between complementary single-stranded polynucleotides. The hybridization reaction can take place when the capture polynucleotide is in a solution or, alternately, the capture polynucleotide can be attached directly or indirectly to a support such as nylon, nitrocellulose, polystyrene or a similar support material prior to carrying out the hybridization reaction. Typically, only unlabeled capture polynucleotide is directly attached to a support because the charged hapten label of a polynucleotide directly attached to a support would not be "visible" to the detection reagents.

"Detecting" the label means that either the presence of the charged hapten label is determined, or the concentration of the charged hapten label in solution is determined as a measure of the concentration of the charged hapten label originally present. The term "detecting" also refers to detecting either the charged hapten label of hybridized probe and/or the charged hapten label of nonhybridized probe.

Detection of the label can be carried out with an immunological system that uses one or two antibodies. In a single antibody system the first antibody is conjugated to a detectable moiety. In a two-antibody detection system the second antibody is usually conjugated to the detectable moiety. The detectable moiety allows the presence of the charged hapten label to be detected.

The detectable moiety can include an enzyme, enzyme substrate, fluorophore, chromophore, chemilumiphore, and/or one or more haptenic or nonhaptenic labels. Thus the detectable moiety can comprise an enzyme substrate and a biotin label. Conjugating either the first antibody, the second antibody or both to one or more labels such as biotin can allow detection of small amounts of capture polynucleotide quickly with little background noise. In an immunological detection the charged hapten label reacts with an antibody specific to the label. The detection method can be an optical immunoassay, a radioimmunoassay or an enzyme immunoassay, for example. An enzyme immunoassay reaction detection reaction is preferred because of its adaptability to a one- or two-antibody detection system.

The analytical method can include one or more "blocking" steps to assist reduction of the noise resulting from nonspecific binding of the probe polynucleotide. A first blocking step can be carried out before the hybridization reaction to block nonspecific binding sites on the support and on the capture polynucleotide with a blocking means. The blocking means comprises a prehybridization blocking polynucleotide.

A second blocking step can be carried out after the hybridization reaction but before detecting capture polynucleotide with a second blocking means. The second blocking means blocks nonspecific binding sites on the support and on support-fixed compounds such as the capture polynucleotide and other compounds such as fatty acids and carbohydrates that became attached to the support during the incubating step. The second blocking means comprises a posthybridization blocking polynucleotide.

Use of sulfophenyl as the label results in significant advantages. When the label is a sulfophenyl it is possible to detect less than one picogram of capture polynucleotide. Additionally, the capture polynucleotide can be detected in a matter of hours. Furthermore, the nonradioactivity of the sulfophenyl label results in inherently safer procedure, lack of a disposal problem and lack of the risk and cost factors associated with disposal of radioactive labels.

Antibodies to the Charged Hapten Label

In order to detect the charged hapten label, antibodies to the label are used. The antibodies can be polyclonal, monoclonal, and recombinant-DNA-produced antibodies to the charged hapten label. The preferred antibodies are IgG antibodies.

Polyclonal antibodies can be prepared by immunizing an animal such as a goat, rabbit or mouse with an antigen comprising a haptenic sulfophenyl compound conjugated to a carrier to produce an antibody to the hapten. The polyclonal antibody can then be removed from a sample of the animal's body fluid by affinity purification. Rabbit polyclonal antibodies are preferred because they showed higher affinity than goat or mouse polyclonal antibodies for the charged sulfophenyl label.

The antigen can be SPITC-BSA. This antigen comprises a 4-sulfophenylisothiocyanate compound conjugated to bovine serum albumin, a high-molecular-weight carrier. Preferably, the immunization takes place in two stages. In the first stage, the animal is injected with the charged hapten label conjugated to a nonmethylated protein carrier. In the second stage, a booster injection is carried out with the charged hapten label conjugated to a methylated carrier, such as methylated BSA. This two-stage immunization method results in antibodies with a high affinity for the charged hapten label such as the sulfophenyl label.

Monoclonal antibodies can be prepared by the hybridoma methodology taught by G. Kohler and C. Milstein in "Continuous Cultures of Fused Cells Secreting Antibody of Pre-Defined Specificity, "*Nature* 256, 495 (1975) The method comprises immunizing an animal with an antigen comprising the charged hapten label conjugated to a carrier. The animal can be a mammal such as a mouse. Preferably, the immunization is effected with the two-stage nonmethylated/methylated carrier procedure. Monoclonal antibodies prepared by the two-stage immunization procedure showed the highest affinity for the sulfophenyl label.

The hybridoma methodology comprises fusing spleen cells from the immunized animal with myeloma cells, culturing the resulting hybridoma cells in a selective medium, testing for the presence of the desired antibody, and cloning the hybridomas producing the desired antibody.

The hybridomas can be hybrids of a mouse myeloma cell line 653.1 derived from P3X63-Ag8,653 mice and sulfophenyl antigen immunized Balb/c mouse spleen cells. Preferred hybridoma cell lines are identified by Applicant as SPITC AS11, SPITC AS13, SPITC AS14, and SPITC AS15. These cell lines were deposited on Oct. 25, 1989, with the American Type Culture Collection (ATCC) located at 12301 Parklawn Drive, Rockville, Md., 20852, under the provisions of the Budapest Treaty on the International Recognition of the Deposit of Microorganisms for the Purposes of Patent Procedure. The ATCC has assigned these four hybridoma cell lines ATCC deposit numbers HB 10280, HB 10281, HB 10282, and HB 10283, respectively. These hybridoma cultures were tested by the ATCC on Nov. 3, 1989, and determined to all be viable cultures.

Typically, to obtain sufficient amounts of monoclonal antibodies for assay purposes an animal such as a mouse is injected with a solution of the cultured hybridomas. The resulting ascites fluid made by the mouse contains the monoclonal antibodies. The monoclonal antibodies can then be removed by conventional methods.

Antibodies to the charged hapten label can also be made by known recombinant genetics technology. For example, the gene or the relevant portion of the gene of a cell immunized against the sulfophenyl hapten can be removed, and inserted into a suitable host cell. The host cell can then make the antibodies against the charged hapten label.

The recombinant DNA sequence encoding for the antibody to the charged hapten label can be removed from the immunized cell in isolation from the DNA encoding for proteins which normally accompany a DNA sequence. Alternately, the recombinant DNA sequence can be removed from the immunized cell operably linked to control sequences that assist expression of the DNA in the host cell.

Hybridization Probe Kits

Various kits are within the scope of the present invention. A kit for both making the hybridization probe and for detecting the capture polynucleotide can comprise the charged hapten label, the binding moiety, means for catalyzing the attaching reaction, a stopping compound, the first antibody specific to the charged hapten label, the second antibody, the prehybridization reaction blocking polynucleotide, the posthybridization reaction blocking polynucleotide, and one or more control polynucleotides. When the second antibody is present in the kit it is conjugated to the detectable moiety.

The control polynucleotides assist detection of the capture polynucleotide by calibrating the signal received using the SPH-labeled hybridization probe of the present invention. Typically, a positive and a negative control is used. The positive control comprises a polynucleotide labeled with the charged hapten label. The negative control is an unlabeled polynucleotide.

A kit for making the hybridization probe can comprise the charged hapten label, the binding moiety, and means for catalyzing the attaching reaction. The charged hapten label and the binding moiety can be covalently bound together as a tag compound. The tag compound can be a sulfophenylhydrazine compound. The means for catalyzing can comprise a bisulfite salt.

The kit for making the hybridization probe can also include a stopping compound such as an aqueous solution of either a pH-raising buffer or an electrophilic compound.

A kit for detecting the capture polynucleotide can comprise a charged hapten label and an antibody specific to the charged hapten label. The charged hapten label can be the sulfophenyl label, in which case the antibody can be the antisulfophenyl antibody. The kit for detecting can also comprise the binding moiety and means for catalyzing.

The kit for detecting the capture polynucleotide can also comprise the prehybridization reaction blocking polynucleotide, the posthybridization reaction blocking polynucleotide, and one or more control polynucleotides. The kit for detecting capture polynucleotide can optionally also comprise the second antibody.

The detectable moiety can be a fluorescent molecule such as fluorescein isothiocyanate, or an electron-dense compound conjugate such as colloidal gold or ferritin. Alternately, the detectable moiety can be a substrate for an enzyme such as alkaline phosphatase, horseradish peroxidase or a galactosidase. The detectable moiety can be detected by chromogenic, chemiluminescent or fluorescent means. The detectable moiety can be a compound that becomes visible upon reaction with color-developing reagents such as with NBT (nitro blue tetrazolium) and BCIP (5-bromo-4-chloro-3-indolyl phosphate). The kit for detecting can include color-developing reagents.

Protein Probes

The present invention also relates to a protein probe capable of undergoing a specific affinity reaction with a capture molecule. The protein probe comprises the probe protein, the charged hapten label and the binding moiety.

The same charged hapten labels discussed above with respect to hybridization probes can be used for the protein probes. The preferred sulfophenyl label of the protein probe can be recognized by the antisulfophenyl antibody, as demonstrated by Example 12 and FIG. 9.

The binding moiety attaches the probe protein to the charged hapten label. The binding moiety can be selected from the group consisting of a succinimides, maleimides, halogens, hydrazines, primary, secondary and tertiary amines, amides and derivatives thereof.

The probe protein is capable of undergoing a specific affinity reaction with a capture molecule. The specific affinity reaction generally involves noncovalent bonding and has an affinity comparable to the affinity of a typical antigen-antibody interaction. Typical probe protein/capture molecule pairs include antigen/antibody; protein receptor/hormone; and enzyme/enzyme inhibitor.

The protein probe of the present invention provides an alternative to currently available nonradioactive protein probes. The protein probe can be used to assist detection of a variety of capture molecules. The capture molecule can be, for example, an antibody, antigen, hormone, steroid, carbohydrate, enzyme inhibitor, enzyme effector, various enzyme substrate analogues, and a nucleic acid.

Method for Making the Protein Probe

A method for making the protein probe in accordance with the present invention comprises selecting the charged hapten label, the binding moiety, and the probe protein. Preferably, the charged hapten label and the binding moiety are covalently bound to each other as the tag compound. The binding moiety of the tag compound is attached to the probe protein in the attaching reaction. The attaching reaction can be carried out in a suitable container by adding a solution of the probe protein to a solution of the tag compound. The attaching reaction is stopped with the stopping compound.

An illustrative protein probe can be made by combining a sulfophenylisothiocyanate (SPITC) tag compound with the probe protein in the attaching reaction. Many of the known reactions for attaching a biotin label to a protein or the carbohydrate portion of a protein can be used to attach the charged hapten label. Thus, for example, the nitrohydrosuccinimide (NHS), sulfo-NHS ester, maleimide, active halogen, hydrazine and hydrazide reaction schemes can be used.

Method for Detecting the Capture Molecule

A method for detecting the capture molecule in accordance with the present invention comprises mixing the protein probe and the capture polynucleotide, incubating the mixture, separating protein probe bound to the capture molecule from protein probe not bound to the capture molecule, and detecting the capture molecule. The capture molecule is detected by detecting the charged hapten label of either bound or unbound protein probe by an immunological detection means. In an immunological detection the charged hapten label reacts with the antibody specific to the charged hapten label.

Protein Probe Kits

A kit for making the protein probe and for detecting the capture molecule in accordance with the present invention comprises the charged hapten label, the binding moiety, means for catalyzing the attaching reaction, the first antibody specific to the charged hapten label, the second antibody conjugated to a detectable moiety, and means for detecting the detectable moiety.

A kit for making the protein probe in accordance with the present invention comprises the charged hapten label, the binding moiety and means for catalyzing the attaching reaction.

A kit for detecting the capture molecule in accordance with the present invention comprises the charged hapten label and the antibody specific to the charged hapten label. The kit for detecting can also comprise a first anti-charged hapten label antibody, a second antibody directed against the first antibody, the second antibody being conjugated to the detectable moiety, and means for detecting the detectable moiety.

EXAMPLES

The following examples are set forth as illustrations of various features and embodiments of the invention and are not intended to limit the scope of the claimed invention.

Example 1

(Comparison of Ammonium Sulfite and Sodium Bisulfite Catalysis of the Attaching Reaction)

Ammonium sulfite and sodium bisulfite were used to catalyze the attaching reaction of SPH to M13 DNA. Two solutions were prepared. Solution (A) contained 10 mg/ml of SPH, 1 mg/ml hydroquinone, and 2.0M $(NH_4)_2SO_3$ adjusted to pH 4.5. Solution (B) contained 10 mg/ml SPH, 1 mg/ml hydroquinone, and 2.0M $Na_2S_2O_5$ adjusted to pH 4.5. The two solutions were heated to 80° C. prior to the addition of single-stranded M13 DNA to a concentration of 1 μg/ml as the probe polynucleotide. At each of the six time points (3, 6, 10, 15, 20, and 30 minutes), samples were withdrawn and the attaching reaction was stopped by the addition of 9 volumes of 1.0 Tris HCl (pH 8.5) as the stopping compound. These samples were further diluted in order that 5 ng and 50 pg of DNA each time point could be loaded directly onto an agarose gel for electrophoresis. The samples were electrophoresed for about two hours prior to blotting onto nitrocellulose. The blots were baked for 2 hours at 80° C. under vacuum and then detected prior to detection with rabbit affinity-purified antisulfophenyl antibody. (See Examples 2 and 3 for the method for producing this antibody).

The results of this study are provided in FIG. 2. In spite of the short development time (10 min with the color-developing reagents BCIP and NBT), the sodium bisulfite-treated samples allowed detection of the 50 pg of labeled DNA after only a three-minute attaching reaction. A three-minute attaching reaction is therefore sufficient to make sulfophenyl-labeled hybridization probe. The ammonium sulfite solution showed a barely detectable smear with 5 ng of the labeled DNA. The sodium bisulfite solution showed little degradation even after 30 minutes at 80° C., whereas the only detectable DNA in the ammonium sulfite sample had substantially degraded. A clear advantage is therefore revealed to using sodium bisulfite as the attaching reaction catalyst.

Example 2

(Preparation of Polyclonal Antibodies to SPH)

In order to produce antibodies to SPH, a sulfophenyl-isothiocyanate conjugated to bovine serum albumin (SPITC-BSA) antigen was prepared by adding 250 mg of 4-sulfophenylisothiocyanate (SPITC) to a 10 ml solution containing 25 mg/ml Bovine Serum Albumin (BSA) in 50 mM HEPES, pH 8.7. This solution was incubated at 37° C. for 4 hours on a rocking platform prior to dialysis against phosphate-buffered saline (PBS).

Apoferritin was also used as an alternate hapten carrier. A sulfophenylisothiocyanate conjugated to apoferritin (SPITC-Apo) antigen was prepared by the same method used to make an SPITC-BSA antigen. This antigen was used in the ELISA assay of Example 12.

SPITC-BSA at a concentration of 100 μg/ml in PBS was mixed with an equal volume of an adjuvant solution containing 50% complete and 50% incomplete Freund's adjuvant. One-half milliliter of the inoculum was administered intramuscularly to each of two legs of a rabbit. One-tenth milliliter of the inoculum was also administered intradermally to each of ten dorsal sites of the rabbit. Each rabbit was thereby injected with a primary injection of 100 μg of the sulfophenyl antigen. Each rabbit was given a booster injection of 50 μg of the sulfophenyl antigen once a month for several months.

Example 3

(Purification of Polyclonal Antibody to SPH)

The rabbit antisulfophenyl polyclonal antibody raised by the method of Example 2 was affinity purified. SPH bound to affinity gel was prepared by first solubilizing 100 mg of SPH in 30 ml of 0.1M MOPS buffer pH 7.5. Ten milliliters of unwashed Bio-Rad Affi-Gel 10 was then added to the SPH solution. The resulting slurry was allowed to react at room temperature for 2 hours. The reacted slurry was centrifuged at 1500 rpm in a Beckman TJ-6 centrifuge. The supernatant was removed and the remaining gel-pellet was washed exhaustively with distilled water and then with PBS.

Five milliliters of the SPH-bound to the affinity gel was then incubated at 4° C. for 4 hours with 200 ml of pooled rabbit anti-SPH antisera obtained from the method of Example 2. The resulting slurry consisting of the rabbit antisulfophenyl antibody bound to SPH bound to the affinity gel was loaded onto a small Bio-Rad Econo-Column and washed with 100 ml of PBS at 4° C.

Hapten displacement chromatography was then used to remove the rabbit antisulfophenyl polyclonal antibody bound to the SPH-Affi-Gel 10 column. The haptenic displacement group was a succinylated derivative of SPH. The succinylated derivative of SPH was prepared by incubating at room temperature for one hour 10 gm SPH with 10 gm of succinic anhydride in a solution containing 25 ml of 10X PBS and approximately 200 ml of distilled water. After the incubation 30 ml of 1.0M Tris HCl (pH 7.5) was added. This solution was further incubated for 2 hours at 37° C. The final volume was adjusted to 250 ml to obtain a solution of 1X PBS, 120 mM Tris HCl and 200 mM of the SPH-succinate. Ten milliliters of this displacement mixture was incubated with the rabbit antisulfophenyl antibody bound to SPH bound to affinity gel slurry for 60 minutes at 4° C. and then dialyzed against PBS for 3 days at 4° C. This method provided purified polyclonal antisulfophenyl antibody.

Example 4

(Preparation of Hybridization Probe)

A hybridization probe was made by attaching sulfophenylhydrazine to a cytosine base-containing nucleic acid in an attaching reaction. The sulfophenylhydrazine was used in a labeling mix. The reagents used to prepare the labeling mix were:

SPH dry "crystals" (sulfophenylhydrazine, phenylhydrazine-4-sulfonic acid hemihydrate, available from Fluka as #78720-powder, 99% pure);

sodium bisulfite (sodium metabisulfite, Sigma #s-9000);

hydroquinone solution (100 mg/ml in ethanol, stored at −20° C.); and 1.0M sodium citrate solution (pH 5.2).

The labeling mix was prepared by dissolving 0.9505 grams of the sodium metabisulfite ($Na_2S_2H_5$) in 4.2 ml of distilled water. To this bisulfite solution was added 40 mg of the phenylhydrazine-4-sulfonic acid hemihydrate, followed by the addition of 500 ml of the 1.0M sodium citrate solution, pH 5.2. This solution was heated in a water bath at 65° C. until all the reagents were in solution. Fifty microliters of the 100 mg/ml solution of hydroquinone in ethanol was then added.

In order to carry out the attaching reaction, 10 μl of double-stranded pUC SLO plasmid DNA (in Tris or water) was first denatured by being boiled in water for about 5 to 10 minutes. Denaturing provided single-stranded pUC SLO plasmid DNA to use as the probe polynucleotide. Ninety microliters (9 parts) of the labeling mix was then quickly added to 10 μl (1 part) of the denatured DNA solution. This mixture was incubated at 80° C. for 10 minutes. The attaching reaction was stopped by the addition of 50 μl (5 parts relative to a starting DNA volume of 10 μl) of 3.0M Tris (pH 8.5) as the stopping solution. The mixture of hybridization probe, labeling mix and probe polynucleotide can be dialyzed to remove unreacted hapten and catalyst or used directly in a hybridization reaction with a capture polynucleotide.

Example 5

(Hybridization Reaction)

A hybridization reaction between the sulfophenyl-labeled salmon sperm hybridization probe of Example 4 and a capture polynucleotide consisting of denatured pUC SLO plasmid DNA was then carried out. The denatured pUC SLO DNA was blotted onto nitrocellulose supports. A prehybridization reaction blocking step was performed to the pUC SLO DNA and to the nitrocellulose support using a standard prehybridization mix comprising 5X SSPE, 50% formamide, 5X Denhardts, 100 µg/ml denatured salmon sperm DNA (phenol extracted and sonicated) and 0.1% SDS. The prehybridization blocking step was performed at 37° C. for at least an hour.

Hybridization of the sulfophenyl-labeled pUC SLO DNA hybridization probe and the support-fixed pUC SLO DNA as the capture DNA was set up in 5X SSPE, 50% deionized formamide, 5X Denhardts and 100 µg/ml denatured salmon sperm DNA. Hybridization was performed at 37° C. in a shaking incubator. Hybridization probe concentrations between 50 ng/ml to 1 µg/ml can be used. Large volumes of hybridization probe such as about 0.2 ml/cm$^2$ were used because it was easier to work with large hybridization probe volumes.

Example 6

(Detection of Hybridized pUC SLO DNA)

Hybridized probe was detected using the rabbit antisulfophenyl polyclonal antibody of Example 3 in an enzyme-based colorimetric precipitation reaction. The blots on the nitrocellulose supports obtained from Example 5 were washed in a stringency wash with three 10-minute changes of a 0.1X SSPE buffer at 65° C. The stringency wash separated hybridized from nonhybridized polynucleotide.

The blots remaining on the nitrocellulose supports were then treated with a posthybridization reaction blocking step to block nonspecific binding sites on the support and on compounds that had become attached to the support during the hybridization step, by incubating the washed blots in a 1X wash buffer for 30 minutes at 23° C. or 37° C. in a shaking incubator. The 1X wash buffer comprised 100 mM NaCl, 10 mM Tris HCl (pH 7.5), 1 mM EDTA, 0.5% NP 40, 0.1% dextran sulfate, and 500 µg/ml phenol extracted whole (cheap) yeast RNA.

The blots were then incubated with the affinity-purified rabbit antisulfophenyl antibody obtained from Example 3, at a concentration of 0.1 µg/ml in the 1X wash buffer. The incubation was carried out at 37° C. for about 45 minutes. Unbound rabbit antisulfophenyl antibody was then rinsed away with a two brief washes in the 1.0X wash buffer. The blots were then washed with an alkaline salt wash buffer for about 5 minutes. The alkaline salt wash buffer comprised 1.0M NaCl, 100 mM Tris HCl (pH 10), and 50 mMMgCl$_2$.

The alkaline salt wash buffer was then rinsed off the blots using a couple of brief washes of the 1.0X wash buffer at 37° C.

The second antibody, a 1:2000 dilution of commercially available goat anti-rabbit alkaline phosphatase conjugate, in 1.0X wash buffer was then added to the blots followed by incubation at 37° C. for about 45 minutes. The blots were then rinsed with the 1.0X wash buffer at 37° C. A further rinse for approximately 10 minutes was then carried out with an alkaline phosphatase buffer at 37° C. The alkaline phosphatase buffer comprised 100 mM Tris pH 9.5, 100 mM NaCl, and 50 mM MgCl$_2$.

A detection solution was then added to a CLAVIE bag (Bel Art Products), followed by incubation at 36° C. for about 2 hours. Incubation can be carried out for between about 30 minutes to about 12 hours to achieve a desired color intensity. The detection solution used consisted of 10 µl of Nitro Blue Tetrazolium (100 mg/ml in 50% DMF), 10 µl of 5-Bromo 4-Chloro 3-Indolyl Phosphate (50 mg/ml in DMF), and 3 ml of the alkaline phosphatase buffer. The detection reaction was stopped by rinsing with distilled water and Tris HCl, followed by air-drying and photographing the blots. The presence of the colored blots showed the presence of the sulfophenyl-labeled pUC SLO DNA hybridization probe hybridized to the complementary pUC SLO DNA. Detection of the pUC SLO capture DNA was thereby achieved.

Example 7

(Preparation of Hybridomas)

Hybridomas capable of making monoclonal antibody with a specific affinity for a sulfophenyl label were prepared. The materials used were as follows. The myeloma cells used were derived from the P3X63-Ag8.653 myeloma cell line, a non-secreting mouse myeloma line developed by Kearney et al., *J. Immunol*, 123:1548 (1979). The spleen cells used were taken from Balb/c mice immunized by the procedure set forth below. The growth media was DME low glucose (Irvine Scientific), supplemented with 10% fetal calf serum (Hyclone) and 2 mM 1-glutamine (Irvine Scientific). The used media was growth media from a three-day culture of 653.1 cells, centrifuged and filtered to remove cells. The CHAT Media was 50% growth media and 50% conditioned media with 100 units/ml of penicillin-streptomycin solution (Irvine Scientific), $4\times10^{-7}$M aminopterin (Sigma), $1\times10^{-4}$M hypoxanthine (MA Bioproducts), $1.6\times10^{-5}$M thymidine (MA Bioproducts), and 10 units/ml insulin (Eli Lily). The conditioned media was 50% growth media—50% used media and $2.5\times10^{-5}$M b-mercaptoethanol (Sigma). Polyethylene glycol (PEG) with a molecular weight between about 1300 and 1600 (Sigma) was used. The injection media was DME low glucose with 100 units/ml penicillin-streptomycin solution. One-half milliliter of Pristane (2,6,10,14-tetramethylpentadecane, available from Aldrich) was injected intraperitoneally into each Balb/c mouse two weeks prior to hybridoma injection.

The hybridomas were made using the method developed by Kohler and Milstein, *Nature* 256:495 (1975). The spleen from the immunized mouse was aseptically removed after cervical dislocation and was ground in a tissue sieve until a single-cell suspension was obtained. After washing, the cells were mixed with the washed 653.1 myeloma cells in a 2:1 ratio of spleen to myeloma cells and then pelleted. The supernatant was removed and the PEG added slowly over one minute. PBS was added to bring the total volume to 22 ml and the cells were then pelleted for 8 min after the start of the PEG addition. The pellet was resuspended in 200 ml of CHAT media and 0.2 ml of the suspension was added to each well of ten 96-well microtiter plates. The wells were supplied with fresh CHAT on day 6 or 7 postfusion.

Testing of the wells for growth began on day 10 and continued over the next 3–4 days. Wells with an optical density reading greater than the negative control were retested on the following day. If the reading remained greater than the negative control on the second day of testing, the colony was considered positive and was cloned. Cloning was carried out by limiting dilution in conditioned media into two 96-well plates, one with 5 cells/well and one with 1 cell/well. One week after cloning, single-colony wells were tested by enzyme immunoassay (EIA). If all wells were positive, the line was considered pure and was recloned a second time for stability. If all the wells did not test 100% positive, a positive well was used for the second cloning. The plates were again tested 7 days after the cloning. This procedure was repeated until all the clones tested 100% positive. The cells were then expanded in growth media and injected in injection media into the peritoneal cavity of Pristane-primed Balb/c mice at a concentration of about $3\times10^6$ hybridoma cells per mouse.

Prior to injection, supernatant from the cultured cells was used for isotyping by the Ouchterlony gel diffusion method, *Acta Path Microbiol Scand* 26:507 (1949). Ascites fluid was harvested from the mice about 10 days after the mice had been injected with the hybridoma cells. The ascites fluid was then titered by EIA, and the IgG isotype content was measured using a Beckman ICS rate nephelometer.

The SPITC AS11 mice were immunized as follows. Fifty micrograms of SPITC-BSA in Freund's complete adjuvant (FCA) was injected intraperitoneally followed at 10 weeks by intraperitoneal injection with 150 µg of methylated SPH-DNA, followed by intraperitoneal injection of BSA in Freund's incomplete adjuvant (FICA). One month later, 150 µg of methylated SPH-DNA was injected intraperitoneally, followed by intraperitoneal injection of BSA in FICA. One month later, 20 µg of methylated SPH-DNA/methyl was injected intraperitoneally. Finally, on the date of fusion, BSA in saline was administered intravenously.

The SPITC AS13, SPITC AS14, and SPITC AS15 mice were immunized as follows. Fifty micrograms of SPITC-BSA in Freund's complete adjuvant (FCA) was injected intraperitoneally followed at 10 weeks by intraperitoneal injection with 100 µg of methylated SPH-DNA, followed by intraperitoneal injection of BSA in Freund's incomplete adjuvant (FICA). One month later, 100 µg of methylated SPH-DNA was injected intraperitoneally, followed by intraperitoneal injection of BSA in FICA. One month later, 20 µg of methylated SPH-DNA/methyl was injected intraperitoneally, followed by intravenous injection of BSA in saline. Three weeks later, 20 µg of methylated SPH-DNA was injected. Finally, three days prior to fusion, BSA in saline was administered intravenously.

The methylated SPH-DNA antigen was prepared as follows. Calf thymus DNA (10 mg/ml) was labeled with SPH by the following procedure: (a) 10 ml of calf thymus DNA was denatured by heat at 100° C. for 15 minutes; (b) 90 ml of the SPH labeling mix of Example 6 was the mixture was incubated at 80° C. for 20 min prior to dialysis against PBS. The sulfophenyl-labeled DNA was then combined with methylated BSA following the procedure described by Johnston et al. in *Biochemistry* 22, 3453–3460 (1983).

The hybridomas prepared by this method were capable of producing monoclonal antibody with a specific affinity for the sulfophenyl label.

Example 8

(Detection of Less Than One Picogram of Capture Polynucleotide)

Detection of a very small amount of capture polynucleotide is possible using the hybridization probe according to the present invention as shown by FIG. 5. FIG. 5 sets forth the endpoint hybridization or sensitivity of a sulfophenyl-modified pUC SLO plasmid hybridization probe for calf thymus DNA target polynucleotide.

A nitrocellulose strip was spotted on the top row of the strip with twelve 2 µl control spots containing from left to right, (a) the calf thymus DNA capture polynucleotide at concentrations of 1 µg, 333 ng, 111 ng, 37 ng, 12 ng, 4 ng, 13 ng, 457 pg, 152 pg, 50.8 pg, 16.9 pg and 5.6 pg, and (b) the unlabeled pUC SLO plasmid DNA probe polynucleotide at concentrations of 40 ng down to 0.22 pg, as shown on the strip. The nitrocellulose strip was also spotted on the bottom row with twelve spots containing the hybridization probe hybridized to the calf thymus DNA capture (target) polynucleotide.

The hybridization probe was prepared as follows. Ten microliters of the pUC SLO plasmid DNA was boiled for 10 minutes to obtain a solution containing 3 micrograms of single-stranded pUC SLO for use as the probe polynucleotide. Ninety microliters of the SPH labeling mix was added to the solution of the probe polynucleotide. The attaching reaction was carried out for 10 minutes at 80° C. before being stopped by adding 40 µl of 2.0M succinic anhydride (in 100% dimethylformide) as the electrophilic stopping compound. The entire stopped attaching reaction solution (including the labeling mix and the SPH-labeled hybridization probe) was then added to a hybridization buffer solution. The hybridization buffer solution comprised 5X SSPE, 50% formamide, 5X Denhardts, and 100 µg/ml of the calf thymus DNA capture polynucleotide. The mixture was incubated overnight at 37° C. before being spotted on the bottom row of the nitrocellulose strip at the indicated twelve capture or target polynucleotide concentrations. The washing and detection steps were performed as set forth in Example 6, using the protein affinity-purified AS14 monoclonal antibody as the first or primary antisulfophenyl antibody. An enzymatic detection was allowed to proceed for 2 hours at room temperature.

As set forth by FIG. 5 the sulfophenyl-labeled hybridization probe used according to the invention made possible the detection of 0.22 pg of the capture polynucleotide.

Example 9

(Detection of *Legionella pneumophila* DNA)

A sulfophenyl-labeled hybridization probe was used to detect Legionella pneumophila capture polynucleotide by direct labeling of whole denatured bacterial DNA. Whole DNA was derived from six different Legionella species: *L. pneumophila, L. spiritensis, L. feeleii, L. gormani, L. crythra,* and *L. anisa.* These six different types of Legionella DNA were denatured and spotted, in a row numbered 1 to 6, in the order given above onto five nitrocellulose strips at concentrations of 20 ng/spot, as set forth by FIG. 6. The six different support-fixed single-stranded Legionella DNA therefore served as six different possible capture polynucleotides.

Five different concentrations (1000 ng, 100 ng, 10 ng, 1 ng, and 0.1 ng) of *Legionella pneumophila* DNA were then labeled with SPH as follows. Five samples of 10 μl of water containing the indicated quantity of *Legionella pneumophila* DNA (1000 ng, 100 ng, 10 ng, 1 ng or 0.1 ng) were boiled for 10 minutes to denature the DNA. Ninety microliters of the SPH labeling mix was then added and the five mixtures were incubated at 80° C. for 10 minutes prior to the addition of 40 μl of 2.0M succinic anhydride to each of the mixtures as the stopping compound. Each mixture (the labeling mix and the sulfophenyl-labeled hybridization probe) was then added to the designated nitrocellulose strips, numbered vertically from 1 to 5.

The hybridization reaction was carried out overnight. The hybridization and detection methodology was as previously described in Examples 5 and 6. A high stringency wash (0.1X SSPE at 65° C.) was performed prior to the detection as set forth in Example 6. Enzymatic detection was continued for 2.0 hours at room temperature. The results are shown in FIG. 6.

As indicated by FIG. 6 the sulfophenyl-labeled *Legionella pneumophila* hybridization probe specifically hybridized with the complementary *Legionella pneumophila* capture polynucleotide. Detection of *Legionella pneumophila* DNA was therefore achieved.

Example 10

(Affinity of Monoclonal Antibodies for the Sulfophenyl Label of a Hybridization Probe)

A comparison was made of the affinity of the mouse monoclonal antisulfophenyl antibodies made by nine different hybridoma cell lines of the invention for the sulfophenyl label.

Sulfophenyl-labeled pUC SLO DNA was directly spotted onto nitrocellulose support strips at concentrations of 16,4 ng, 5.46 ng, 1.82 ng, 0.60 ng, 202 pg, 67.5 pg, 22.5 pg, 7.5 pg, 2.5 pg, 0.8 pg, and 0.27 pg. Because the labeled DNA was spotted directly from the labeling mix prepared according to Example 4, some free SPH attached to the nitrocellulose and was detected as the colored outer rings seen prominently, for example, on the AS16 strip. The detection of the sulfophenyl-labeled DNA was carried out by using the dual-antibody detection method described in Example 6.

The affinity and therefore the sensitivity for the sulfophenyl label was greatest for the mouse monoclonal antibodies derived from the AS11, AS13, AS14 and AS15 hybridoma cell lines as indicated by FIG. 7. These four samples of mouse monoclonal antibody also showed low affinity for the free SPH as evidenced by the absence of the outer rings from the blots. The AS11, AS13, AS14, and AS15 hybridoma cell lines were deposited with the ATCC.

Example 11

(Detection of Capture Polynucleotide in Situ)

In Situ detection of HPV 6 DNA was accomplished using a sulfophenyl-labeled hybridization probe in accordance with the present invention. This allowed detection of an HPV 6 induced lesion in a human cervical biopsy specimen.

The hybridization probe was prepared as follows. HPV 6 DNA was CsCl-purified to obtain a 1 mg/ml concentration of double-stranded HPV 6 DNA. Five hundred microliters of the HPV 6 DNA was then sonicated using a Heat-Systems Sonicator with a microtip probe. Sonication was continued for 1 minute with a 10% output at a setting of about 1.5. Following sonication, the DNA was denatured by being boiled in water bath for 5 minutes. The denatured HPV 6 DNA was then labeled with SPH by the attaching reaction. Following the attaching reaction, the sulfophenyl-labeled single-stranded HPV 6 DNA was dialyzed exhaustively against T.E. (10 mM Tris HCl pH 7.5, 1 mM EDTA).

HPV 6 DNA in the human cervical biopsy tissue sample was denatured in situ by application of 2X SSC and 50% formamide at 70° C. The hybridization reaction was carried out for 12 hours at 42° C. in 4X SSC and 40% formamide. The sulfophenyl-modified probe was used at a concentration of 5 μg/ml. The primary antibody was the affinity-purified rabbit antisulfophenyl antibody (2.3 μg/ml) of Example 5. The second antibody was the alkaline phosphatase-conjugated goat anti-rabbit antibody (Chemicon 1:2000).

The results of the enzyme-based colorimetric precipitation reaction used to detect hybridized probe are set forth in FIG. 8. The dark circular areas are sites of sulfophenyl-labeled HPV 6 DNA hybridization probe hybridized to HPV 6 capture DNA. Thus the sulfophenyl label hybridization probe made possible in situ detection of complementary HPV 6 capture DNA in the tissue specimen.

Example 12

(Detection of a Sulfophenyl Label of a Protein Probe)

The detection of the sulfophenyl label of a protein probe by monoclonal antibodies was determined using a standard ELISA (enzyme-linked immunosorbent assay) microtiter assay. The ELISA assay allowed detection of the immunological reaction of the monoclonal antibodies with the sulfophenyl label of the protein probe. The ELISA assay is essentially a sandwich immunoassay in which the first antibody is the monoclonal antibody of the invention and the second antibody is the commercially available conjugate antibody.

The reagents used to conduct the standard ELISA assay included:

a. The SPITC-Apoferritin antigen (SPITC-Apo) at a concentration of 1 μg/ml (1:12,000), prepared by the method of Example 2.

b. A carbonate-bicarbonate, pH 9.6 coating buffer.

c. Four sets of ascites fluid containing respectively monoclonal antibodies obtained from injection of mice with the AS11, AS13, AS14, and AS15 hybridoma cell lines. Each of the four monoclonal antibody solutions was used with separate microtiter plate test and were serially diluted (X2) on the plate from dilution #1 (1:100) to dilution #24 (1:838, 860,800).

d. The controls used were normal mouse ascites serum (NAS) used at a dilution of 1:100, Used media, and the positive control was Ascites #6 (1:100).

e. The second antibody used was rabbit antimouse antibody conjugated to alkaline phosphatase (available from Sigma as #57F-8824), used at a dilution of 1:12,000.

f. Alkaline phosphatase substrate was prepared from phosphatase substrate, p-nitrophenyl phosphate (Sigma 104-0), and a diethanolamine buffer.

g. Linbro/Titertek microtiter plates were used (Cat. #76-381-04).

The assay was carried out by preparing a predetermined dilution of antigen (SPITC-Apo) in cold coating buffer and keeping it on ice. About 200 µl of the diluted antigen was dispensed to the plate wells using a multichannel pipette. Each of the four fluid samples of monoclonal antibody was added to the wells of a separate plate in a serial dilution. The plates were then incubated for about 2 hrs at about 37° C.

The second antibody was added to the wells. After further incubation and washing, diluted substrate (1 mg/ml in the diethanolamine buffer) was added. Incubation for about 30 minutes at about 37° C. followed. The results were read with a Titertek spectrophotometer set at 405 nm.

The results of the ELISA assay are graphically shown by FIG. 9. Triplicate titers of each of the four monoclonal antibody containing ascites fluids were used to obtain the data shown in FIG. 9. An absorbance (ABS) value greater than the normal mouse ascites serum (NAS) baseline indicates binding of the monoclonal antibody to the sulfophenyl label of the protein probe. The AS13 monoclonal antibodies showed the highest affinity for the sulfophenyl label of the protein probe at all dilutions used.

Example 13

(Methods for Preparation of Complexes Useful for Detection of Capture Polynucleotide and Capture Molecule)

This Example presents three methods for the preparation of antisulfophenyl antibody complexes. The complexes can include a variety of detectable moieties such as an enzyme, enzyme substrate and/or a haptenic or nonhaptenic label. The complexes can be used after capture polynucleotide and capture molecule have reacted with a sulfophenyl-labeled probe to detect smaller amounts of capture polynucleotide and capture molecule. Additionally, use of the complexes can make possible faster detection of capture polynucleotide and capture molecule with less background noise.

Method A (Preparation of Enzyme-conjugated Antisulfophenyl Antibody)

This is a method for the preparation of a complex comprising a primary antisulfophenyl antibody conjugated directly to alkaline phosphatase. Other enzymes such as horseradish peroxidase can also be used.

The complex can be made using a coupling procedure modified after that disclosed by E. Harlow et al. in *Antibodies, A Laboratory Manual*, chapter 9, pages 346–347 ("Glutaraldehyde Coupling"), Cold Spring Harbor Laboratory (1988) as follows:

a. Mix 10 mg of purified antisulfophenyl antibody with 5 mg of alkaline phosphatase to obtain a 1 ml mixture of antibody and enzyme.

b. Dialyze the mixture against four changes of 0.1M sodium phosphate buffer (pH 6.8).

c. Transfer the enzyme-antibody mixture to a container which allows easy and efficient stirring of the small volume. Slowly add 0.05 ml of a 1% solution of glutaraldehyde.

d. After 5 minutes, switch off the stirrer and allow to sit at room temperature for 3 hours. Add 0.1 ml of 1.0M ethanolamine (pH 7).

e. After 2 more hours, dialyze overnight at 4° C. against three changes of PBS.

f. Spin the mixture at 40,000 g for 200 min.

g. Store the supernatant at 4° C. in the presence of 50% glycerol, 1 mMMgCl$_2$, 1 mM ZnCl$_2$, 0.02% Na azide.

The supernatant contains antisulfophenyl antibody conjugated to alkaline phosphatase. This complex can be used to detect the sulfophenyl label of a nucleic acid probe or of a protein probe. Improved detection of smaller amounts of sulfophenyl label can be possible because the enzyme is delivered directly to the site of the sulfophenyl label.

Method B (Preparation of Labeled Antisulfophenyl Antibody)

This is a method for the preparation of a complex comprising an antisulfophenyl antibody conjugated to a biotin label. Other labels such as fluorescent and chemiluminescent labels could also be used. The complex can be prepared as follows:

a. Prepare a solution of N-hydroxysuccinimide-X-Biotin at 10 mg/ml in dimethyl sulfoxide.

b. Prepare an antisulfophenyl antibody solution of approximately 1–3 mg/ml in sodium bicarbonate buffer at about pH 8.0. Dialyze away all reactive amines.

c. Add the biotin ester to the antisulfophenyl antibody at a ratio of approximately 10–250 µg of biotin-NHS ester per milligram of antibody. The NHS-ester should be added with stirring at 4° C.

d. Incubate at 4° C. for a minimum of 3 hours.

e. Dialyze the antibody-biotin mixture against phosphate-buffered saline.

The biotin-tagged antisulfophenyl antibodies prepared by this method can be detected using compounds that have a specific affinity for biotin such as streptavidin-alkaline phosphatase, anti-biotin-alkaline phosphatase or other enzyme conjugates. This method can allow improved detection of sulfophenyl label because using a labeled primary antibody allows more detectable labels such as biotin labels to be delivered to the vicinity of the sulfophenyl label.

Method C (Preparation of Sulfophenyl-labeled Enzyme)

This is a method for the preparation of a complex comprising an antisulfophenyl antibody—sulfophenyl-labeled alkaline phosphatase complex.

The complex can be made using a procedure modified after that disclosed by T. E. Masen et al. in "An Immunoglobulin-Enzyme Bridge Method for Localizing Tissue Antigens," *J. Histochem. Cytochem.* 17:563–569 as follows:

a. Dialyze the alkaline phosphatase against 100 mM sodium carbonate buffer pH 9.0. The concentration of the alkaline phosphatase can be about 2 mg/ml.

b. Dissolve freshly prepared sulfophenyl isothiocyanate in water at a concentration of about 1 mg/ml.

c. Add between 5 and 100 µl of the sulfophenyl isothiocyanate solution to each ml of the alkaline phosphatase.

d. Allow the mixed solution to incubate overnight at 4° C.

e. Dialyze against 50% glycerol, 1 mMMgCl$_2$, 1 mM ZnCl$_2$, 0.02% Na azide, to obtain purified sulfophenyl-labeled alkaline phosphatase.

f. Mix the purified sulfophenyl-labeled alkaline phosphatase with antisulfophenyl antibody. A complex comprising antisulfophenyl antibody—sulfophenyl—labeled alkaline phosphatase is thereby formed.

This complex can be used for improved detection of a capture polynucleotide or capture molecule that has already reacted with a sulfophenyl-labeled probe. Improved detection is possible because use of the complex allows many molecules of alkaline phosphatase to be delivered to the vicinity of the capture polynucleotide or capture molecule.

This example is illustrative of the variety of complexes and methods that can be used to detect a capture polynucleotide or capture molecule that has reacted with, respectively, a sulfophenyl-labeled nucleic acid probe or a sulfophenyl-labeled protein probe. Enzymes, enzyme conjugates, haptens, and nonhaptenic labels different from those set forth but known to the art can be used and are within the scope of this example.

Nucleic acid probes and protein probes according to the present invention have many advantages including the following:

1. Both nucleic acids and proteins can be labeled by the charged hapten labels.
2. The charged hapten labels can be used on the probes in conjunction with other labels such as biotin hydrazide and PHOTOBIOTIN™.
3. Nucleic acids can be labeled in ten minutes or less.
4. No purification of the nucleic acid is required before the nucleic acid is labeled.
5. The preferred charged hapten labels show little non-specific labeling resulting in a low background signal.
6. The capture polynucleotide and the capture molecule can be detected by a nonradioactive immunological detection means.
7. The capture polynucleotide and the capture molecule can also be detected using an immunoradioactive detection method.
8. The nonradioactive immunological detection means are simpler and faster than immunoradioactive detection methods.

The charged hapten labels are inexpensive and stable.

10. Detection of less than one picogram of capture polynucleotide is possible using the charged hapten label and a nonradioactive detection method.
11. The charged hapten label is nonradioactive and therefore safe to use.
12. No complex and time-consuming protein blocking step such as used with biotin labels is required.
13. Disposal of reagents and reaction products is simple and inexpensive when nonradioactive detection means are used.

Although the present invention has been described in considerable detail with regard to certain preferred embodiments thereof, other embodiments within the scope of the teachings of the present invention are possible. For example, a wide variety of charged hapten compounds to use as labels for hybridization probes and for protein probes are possible. The charged hapten label is not restricted to aromatic or to sulfonated compounds. A concomitant wide variety of antibodies is therefore also possible. Accordingly, the spirit and scope of the appended claims should not be limited to the descriptions of the preferred embodiments contained herein.

What is claimed is:

1. A non-radioactive, haptenic probe for detecting a capture polynucleotide comprising:
   (a) a probe polynucleotide, the probe polynucleotide having a polynucleotide sequence substantially complementary to a polynucleotide sequence of the capture polynucleotide;
   (b) at least one non-radioactive, charged hapten label selected from the group consisting of benzoic acid anion, 4-(sulfonyl) benzoic acid anion, and sulfophenyl anion; and
   (c) a hydrazine binding moiety covalently attaching the charged hapten to the N-4 position of a cytosine base of a nucleotide located on the probe polynucleotide wherein detection of the capture polynucleotide is based upon an immunological reaction between the non-radioactive, charged hapten label and an antibody specific to the label.

2. The probe of claim 1 further comprising a spacer compound between the binding moiety and the charged hapten label for separating the charged hapten label from the probe polynucleotide, the spacer compound comprising a linear chain of from about two to about fifteen carbon atoms.

3. The probe of claim 1 wherein the probe polynucleotide comprises single-stranded RNA.

4. The probe of claim 1 wherein the hapten label and the binding moiety comprise a sulfophenylhydrazine compound.

5. The probe of claim 4 wherein the sulfophenylhydrazine compound comprises a 4-hydrazinobenzenesulfonate anion.

6. A hybridization probe comprising a single-stranded DNA or RNA polynucleotide comprising a cytosine base, wherein a 4-hydrazinobenzenesulfonate anion is covalently attached through the hydrazide terminus thereof to the 4-position of the cytosine base.

7. A hybridization probe capable of hybridizing with a capture polynucleotide, the hybridization probe comprising a 4-hydrazinobenzenesulfonate anion covalently attached through its hydrazine terminus to the 4-position of a cytosine base of the probe polynucleotide.

\* \* \* \* \*